United States Patent
Olson

(10) Patent No.: US 11,912,756 B2
(45) Date of Patent: Feb. 27, 2024

(54) MRNA DISPLAY ANTIBODY LIBRARY AND METHODS

(71) Applicant: NantBio, Inc., Culver City, CA (US)

(72) Inventor: Clifford Anders Olson, Culver City, CA (US)

(73) Assignee: NantBio, Inc., Culver City, CA (US)

(*) Notice: Subject to any disclaimer, the term of this patent is extended or adjusted under 35 U.S.C. 154(b) by 424 days.

(21) Appl. No.: 17/236,978

(22) Filed: Apr. 21, 2021

(65) Prior Publication Data

US 2021/0238587 A1 Aug. 5, 2021

Related U.S. Application Data

(62) Division of application No. 16/193,999, filed on Nov. 16, 2018, now Pat. No. 11,015,188.

(Continued)

(51) Int. Cl.
*C40B 40/08* (2006.01)
*C07K 16/00* (2006.01)
(Continued)

(52) U.S. Cl.
CPC .......... *C07K 16/005* (2013.01); *C07K 16/244* (2013.01); *C07K 16/2827* (2013.01);
(Continued)

(58) Field of Classification Search
None
See application file for complete search history.

(56) References Cited

U.S. PATENT DOCUMENTS 9,464,286 B2 10/2016 Zhu et al.
11,015,188 B2 5/2021 Olson
(Continued)

FOREIGN PATENT DOCUMENTS

CA  3 082 172 A1  5/2019
CN  101548034 B  11/2013
(Continued)

OTHER PUBLICATIONS

Examination Report No. 1 received for Australian Patent Application Serial No. 2018367622 dated Jan. 7, 2022, 3 pages.
(Continued)

*Primary Examiner* — Christian C Boesen
(74) *Attorney, Agent, or Firm* — Martin Fessenmaier; Umberg Zipser LLP

(57) ABSTRACT

Compositions, methods and uses of high-diversity nucleic acid library that encodes a plurality of antibodies or antibody fragments are presented. The high-diversity nucleic acid library comprises or is derived from (1) a $V_H$-CDR1/2 sub-library, (2) a plurality of $V_H$-CDR3 sub-libraries, and (3) a $V_L$ sub-library, each of which comprises a plurality of members. Preferably, each member of the sub-libraries comprises at least one random cassette that has a plurality of degenerate base positions. In an especially preferred embodiment, at least portions of at least two members of the $V_H$-CDR1/2 sub-library, the plurality of $V_H$-CDR3 sub-libraries, and the $V_L$ sub-library are recombined to form an expression library member in an expression library, where each member of the expression library encodes a distinct antibody or antibody fragment.

5 Claims, 15 Drawing Sheets

Specification includes a Sequence Listing.

Related U.S. Application Data

(60) Provisional application No. 62/588,914, filed on Nov. 20, 2017.

(51) Int. Cl.
    *C12N 15/10*     (2006.01)
    *C12N 15/62*     (2006.01)
    *C12N 15/11*     (2006.01)
    *C07K 17/00*     (2006.01)
    *C07K 16/24*     (2006.01)
    *C07K 16/28*     (2006.01)
    *C40B 50/06*     (2006.01)
    *C40B 30/04*     (2006.01)

(52) U.S. Cl.
    CPC .......... *C07K 17/00* (2013.01); *C12N 15/1037* (2013.01); *C12N 15/1041* (2013.01); *C12N 15/1062* (2013.01); *C12N 15/111* (2013.01); *C12N 15/62* (2013.01); *C40B 40/08* (2013.01); *C40B 50/06* (2013.01); *C07K 2317/515* (2013.01); *C07K 2317/565* (2013.01); *C07K 2317/622* (2013.01); *C07K 2317/73* (2013.01); *C07K 2317/92* (2013.01); *C07K 2317/94* (2013.01); *C40B 30/04* (2013.01)

(56) References Cited

U.S. PATENT DOCUMENTS

| | | |
|---|---|---|
| 11,034,951 B2 | 6/2021 | Olson et al. |
| 2007/0111260 A1 | 5/2007 | Gao et al. |
| 2012/0202716 A1 | 8/2012 | Horowitz et al. |
| 2013/0030157 A1 | 1/2013 | Prassler et al. |
| 2016/0194627 A1 | 7/2016 | Smider et al. |
| 2019/0153432 A1 | 5/2019 | Olson |
| 2019/0264195 A1 | 8/2019 | Olson et al. |

FOREIGN PATENT DOCUMENTS

| | | |
|---|---|---|
| CN | 111511768 A | 8/2020 |
| JP | 2008-536473 A | 9/2008 |
| JP | 2021-503292 A | 2/2021 |
| KR | 10-2009-0109193 A | 10/2009 |
| KR | 10-2016-0087766 A | 7/2016 |
| KR | 10-1694832 B1 | 1/2017 |
| KR | 10-2020-0075028 A | 6/2020 |
| TW | 201922794 A | 6/2019 |
| TW | I693235 B | 5/2020 |
| TW | 202045548 A | 12/2020 |
| WO | 2006/014498 A2 | 2/2006 |
| WO | 2006/072773 A1 | 7/2006 |
| WO | 2009/085462 A1 | 7/2009 |
| WO | 2010/054007 A1 | 5/2010 |
| WO | 2017/186928 A1 | 11/2017 |
| WO | 2019/099882 A2 | 5/2019 |
| WO | 2020/159524 A1 | 8/2020 |

OTHER PUBLICATIONS

Notice of Allowance received for Canadian Patent Application Serial No. 3,082,172 dated May 2, 2022, 1 page.
Notice of Reasons for Refusal received for Japanese Patent Application Serial No. 2020-527909 dated May 10, 2022, 13 pages. (Including English Translation).
Sidhu et al.,"Phage-displayed Antibody Libraries of Synthetic Heavy Chain Complementarity Determining Regions", J Mol Biol, vol. 338, No. 2, 2004, Apr. 23, 2004, pp. 299-310.
Knappik et al., "Fully Synthetic Human Combinatorial Antibody Libraries (HuCAL) Based on Modular Consensus Frameworks and CDRs Randomized with Trinucleotides", J Mol Biol, vol. 296, No. 1, Feb. 11, 2000, pp. 57-86.
Final Office Action received for Taiwanese Patent Application Serial No. 109109861 dated May 5, 2022, 7 pages. (Including English Translation).
Office Action received for Canadian Patent Application Serial No. 3082172 dated Jun. 10, 2021, 4 pages.
First Office Action received for Taiwanese Patent Application Serial No. 109109861 dated Jan. 13, 2022, 4 pages. (Including English Translation).
Final Office Action received for Taiwanese Patent Application Serial No. 109109861 dated Apr. 26, 2022, 7 pages. (Including English Translation).
Office Action received for Canadian Patent Application Serial No. 3,124,941 dated Sep. 1, 2022, 7 pages.
Request for the Submission of an Opinion received for Korean Patent Application Serial No. 10-2020-7017165 dated Sep. 27, 2022, 6 pages. (Including English Translation).
Notice of Reasons for Refusal received for Japanese Patent Application Serial No. 2020-527909 dated Dec. 2, 2022, 9 pages. (Including English Translation).
First Office Action received for Chinese Patent Application Serial No. 201880074681.2 dated Feb. 24, 2023, 22 pages. (Including English Translation).
Liang et al., "Function blocking antibodies to neuropilin-1 generated from a designed human synthetic antibody phage library", Journal of Molecular Biology, vol. 366, Issue 3, 2007, pp. 815-829.
Hu et al., "Effective Optimization of Antibody Affinity by Phage Display Integrated with High-Throughput DNA Synthesis and Sequencing Technologies", PLoS One, vol. 10, Issue 6, e0129125, 2015, pp. 1-17.
Extended European Search Report received for European Patent Application Serial No. 188782486 dated Jul. 21, 2021, 8 pages.
Chen et al., "Construction of a Human Antibody Domain (V-H)Library", Methods in Molecular Biology, 2009, vol. 525, 15 pages.
Isao et al., "In vitro evolution of single-chain antibodies using mRNA display", Nucleic Acids Research, 2006, vol. 34, No. 19, 8 pages.
Villa et al., "A novel synthetic naive human antibody library allows the isolation of antibodies against a new epitope of oncofetal fibronectin", mAbs, 2011, vol. 3, No. 3, pp. 264-272.
Chen et al., "Preferential germline usage and VH/VL pairing observed in human antibodies selected by mRNA Display", Protein Engineering, Design & Selection, 2015, vol. 28, No. 10, pp. 427-435.
Liu et al. "A Novel Fusion of ALT-803 (Interleukin (IL)-15 Superagonist) with an Antibody Demonstrates Antigen specific Antitumor Responses", The Journal of Biological Chemistry, Nov. 11, 2016, vol. 291, No. 46, pp. 23869-23881.
Airaksinen et al., "Modified base compositions at degenerate positions of a mutagenic oligonucleotide enhance randomness in site-saturation mutagenesis", Nucleic Acids Research, 1998, vol. 26, No. 2, pp. 576-581.
Tiller et al., "A fully synthetic human Fab antibody library based on fixed VH/VL framework pairings with Favorable biophysical properties", mAbs, May 2013, vol. 5, No. 3, pp. 445-470.
Weber et al, "A Highly Functional Synthetic Phage Display Library Containing over 40 Billion Human Antibody Clones", PLoS ONE, Jun. 20, 2014, vol. 9, No. 6, e100000, pp. 1-9.
International Search Report and Written Opinion received for PCT Application No. PCT/US2018/061592, dated Jun. 27, 2019, 12 pages.
Yang et al., "Construction of a large synthetic human scFv library with six diversified CDRs and high functional Diversity", Molecules and Cells, Feb. 2009, vol. 27, No. 2, p. 1-10.
International Search Report and Written Opinion received for PCT Application No. PCT/US2019/016135, dated Oct. 29, 2019, 14 pages.
First Office Action received for Taiwan Patent Application Serial No. 107141333 dated Nov. 4, 2019, 09 pages (Including English Translation).
Amalfitano et al., "Production and Characterization of Improved Adenovirus Vectors with the E1, E2b, and E3 Genes Deleted", Journal of Virology, Feb. 1998, vol. 72, No. 2, pp. 926-933.

(56) References Cited

OTHER PUBLICATIONS

International Preliminary Report on Patentability received for PCT Application No. PCT/US2018/061592, dated Jun. 4, 2020, 08 pages.
Non Final Office Action received for U.S. Appl. No. 16/193,999 dated Dec. 28, 2020, 32 pages.
Non Final Office Action received for U.S. Appl. No. 16/264,304 dated Dec. 28, 2020, 32 pages.
Notice of Allowance received for U.S. Appl. No. 16/193,999 dated Apr. 9, 2021, 21 pages.
Notice of Allowance received for U.S. Appl. No. 16/264,304 dated Apr. 14, 2021, 20 pages.
Notice of Allowance received for U.S. Appl. No. 16/264,304 dated Apr. 28, 2021, 6 pages.
Notice of Acceptance received for Australian Patent Application Serial No. 2018367622 dated Dec. 9, 2022, 3 pages.
Decision to Grant a Patent received for Japanese Patent Application Serial No. 2020-527909 dated May 9, 2023, 6 pages. (Including English Translation).
Notice of Reasons for Refusal received for Japanese Patent Application Serial No. 2021-544556 dated May 19, 2023, 11 pages. (Including English Translation).
Request for the Submission of an Opinion received for Korean Patent Application Serial No. 10-2020-7017165 dated Apr. 28, 2023, 14 pages. (Including English Translation).
First Office Action received for Chinese Patent Application Serial No. 201980090819.2 dated Jun. 2, 2023, 15 pages. (Including English Translation).
Decision to Grant a Patent received for Taiwanese Patent Application Serial No. 109109861 dated Jul. 7, 2023, 4 pages. (Including English Translation).
International Preliminary Report on Patentability received for PCT Application No. PCT/US2019/016135, dated Aug. 12, 2021, 10 pages.
Communication under Rule 71(3) EPC received for European Patent Application No. 18878248.6 dated Oct. 31, 2023, 8 pages.
Notice of Ground of Rejection received for Korea Patent Application No. 10-2021-7025365 dated Nov. 28, 2023, 6 pages (including English Translation).
Reason of Rejection received in Japanese patent Application No. 2021-544556 dated Oct. 27, 2023, 3 pages (including English Translation).

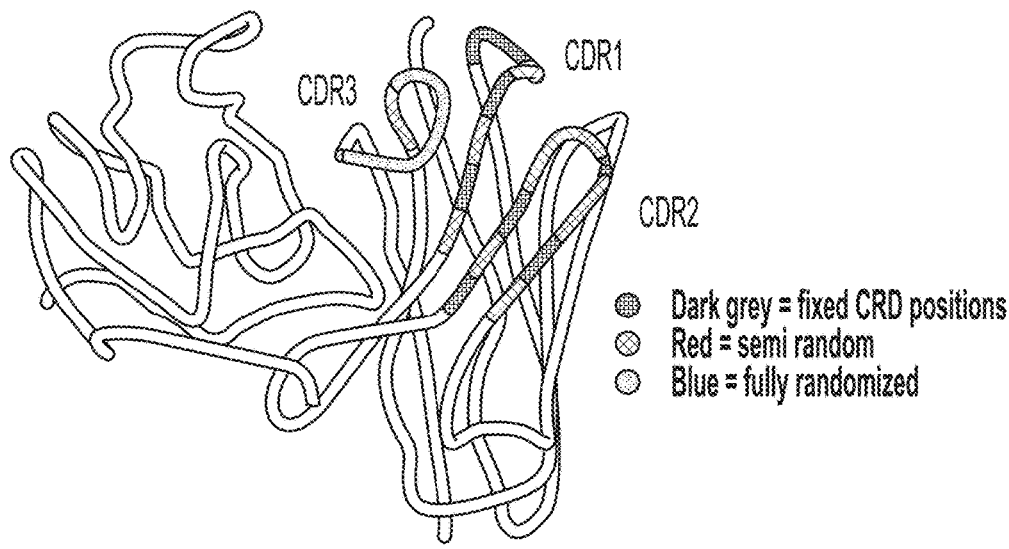

```
CDR1 and 2  GGCTTA GGTCTC A TTTC RVTAGTTACGCTATGCAT TGGG C GAGACG AGGTCTGAACGG   X=TANDSG
            GGCTTA GGTCTC A TTTC TCTRVKTACGCTATGCAT TGGG C GAGACG AGGTCTGAACGG   X=TANKDESRG
• CDR1      GGCTTA GGTCTC A TTTC TCTAGTTACKKGATGCAT TGGG C GAGACG AGGTCTGAACGG   X=GWLV
            GGCTTA GGTCTC A TTTC TCTAGTTACNMTATGCAT TGGG C GAGACG AGGTCTGAACGG   X=SYTN
            GGCTTA GGTCTC A TTTC TCTAGTTACGCTATGAVT TGGG C GAGACG AGGTCTGAACGG   X=STN GGCTTA GGTCTC G TTCA THCATTAGTGGTAGTGGA C GAGACG AGGTCTGAACGG   X=YFS
            GGCTTA GGTCTC G TTCA VKTATTAGTGGTAGTGGA C GAGACG AGGTCTGAACGG   X=VGISLR
            GGCTTA GGTCTC G TTCA GCTATTYGGGGTAGTGGA C GAGACG AGGTCTGAACGG   X=WR
• CDR2-n    GGCTTA GGTCTC G TTCA GCTATTDATGGTAATGGA C GAGACG AGGTCTGAACGG   X=YND+N53
            GGCTTA GGTCTC G TTCA GCTATTAGTNMTAGTGGA C GAGACG AGGTCTGAACGG   X=YSTN
            GGCTTA GGTCTC G TTCA GCTATTAGTKGGAGTGGA C GAGACG AGGTCTGAACGG   X=WG
            GGCTTA GGTCTC G TTCA GCTATTAGTGGTRRTGGA C GAGACG AGGTCTGAACGG   X=DGSN GGCTTA GGTCTC G TGGA RVKAGTACTTAC TACG C GAGACG AGGTCTGAACGG   X=STGANKDE
• CDR2-c    GGCTTA GGTCTC G TGGA GGTNATACTTAC TACG C GAGACG AGGTCTGAACGG   X=YNDH
            GGCTTA GGTCTC G TGGA GGTRVAACTTAC TACG C GAGACG AGGTCTGAACGG   X=TKREAG
            GGCTTA GGTCTC G TGGA GGTAGTACTVRT TACG C GAGACG AGGTCTGAACGG   X=DGNSHR
```

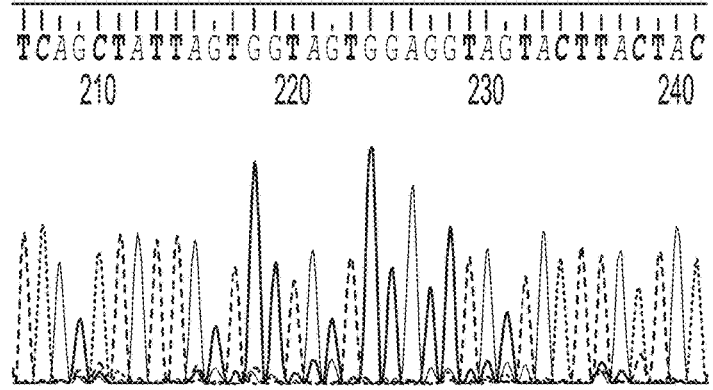

Fig. 2

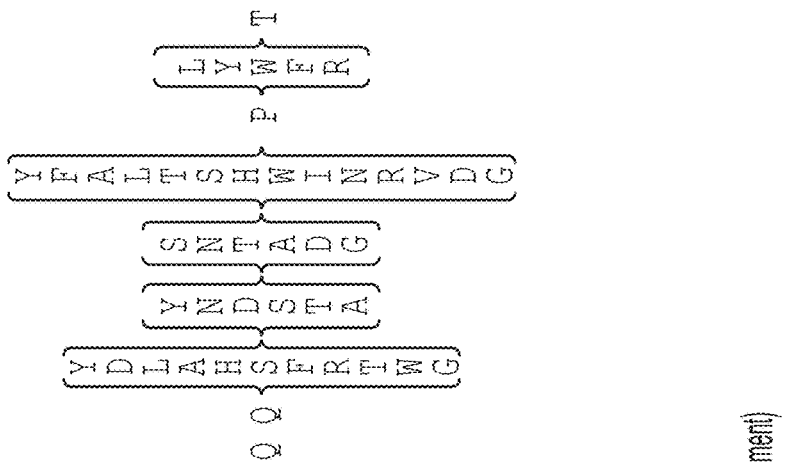

```
CDR L3
RANDL3-1
GGCTTA GGTCTC T GCAG DSG DMT RVT DSG CCT TWC ACTT C GAGACG AGGTCTGAACGG
RANDL3-2
GGCTTA GGTCTC T GCAG BWT DMT RVT DSG CCT TWC ACTT C GAGACG AGGTCTGAACGG
RANDL3-3
GGCTTA GGTCTC T GCAG DSG DMT RVT NWT CCT TWC ACTT C GAGACG AGGTCTGAACGG
RANDL3-4
GGCTTA GGTCTC T GCAG BWT DMT RVT NWT CCT TWC ACTT C GAGACG AGGTCTGAACGG
RANDL3-5
GGCTTA GGTCTC T GCAG DSG DMT RVT DSG CCT YKG ACTT C GAGACG AGGTCTGAACGG
RANDL3-6
GGCTTA GGTCTC T GCAG BWT DMT RVT DSG CCT YKG ACTT C GAGACG AGGTCTGAACGG
RANDL3-7
GGCTTA GGTCTC T GCAG DSG DMT RVT NWT CCT YKG ACTT C GAGACG AGGTCTGAACGG
RANDL3-8
GGCTTA GGTCTC T GCAG BWT DMT RVT NWT CCT YKG ACTT C GAGACG AGGTCTGAACGG
```

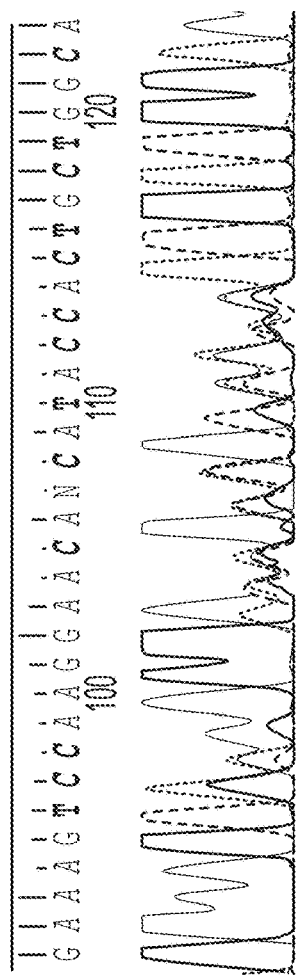

Fig. 4

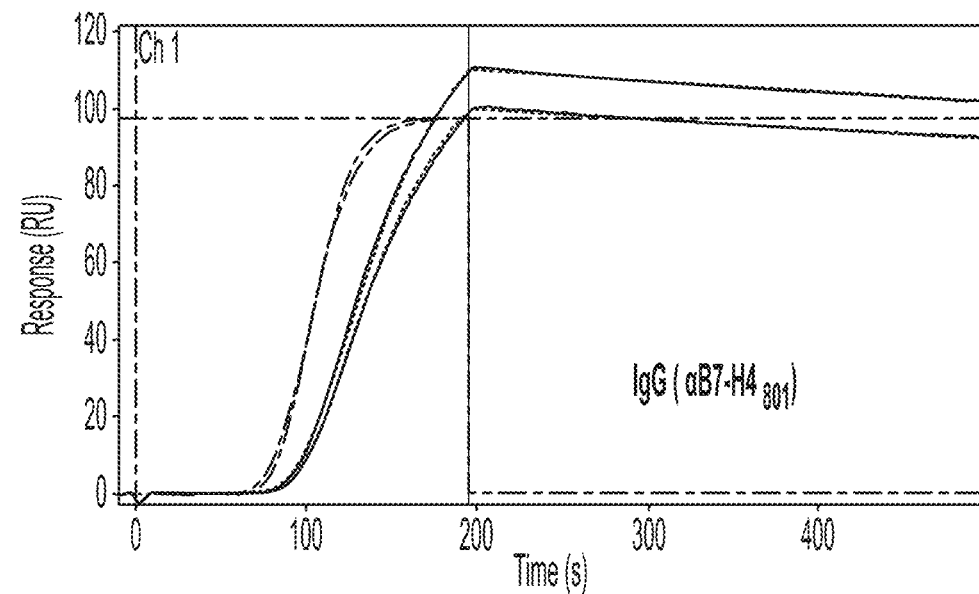
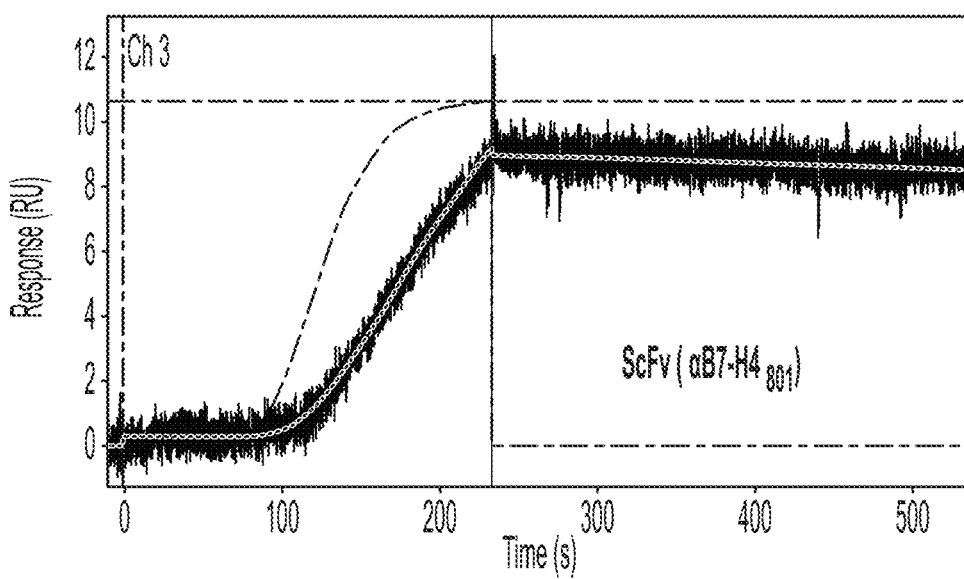
Fig. 10

MRNA DISPLAY ANTIBODY LIBRARY AND METHODS

This application is a divisional application of our allowed co-pending US patent application with the Ser. No. 16/193,999, which was filed Nov. 16, 2018, which claims priority to US provisional patent application with the Ser. No. 62/588,914, which was filed Nov. 20, 2017, both of which are incorporated by reference herein.

FIELD OF THE INVENTION

The field of the invention is compositions and methods for ultrahigh-diversity antibody libraries, especially as it relates to mRNA display libraries and use of mRNA display libraries for generating recombinant high-affinity binders.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Targeting tumor antigens or neoepitopes with high-affinity, specific antibodies or binding molecules has been proven as effective methods for treating cancer patients. As more and more patient-specific and/or cancer specific tumor antigens and/or neoepitopes are identified via in vivo, in vitro, or in silico through omics data analysis, the demand of creating an antibody library or display library that provides high probabilities of selecting antibodies or binders that are stable, soluble, functional, and adaptable has grown. While high-affinity, specific antibodies or binding molecules can be identified among or derived from natural antibody pools, such identified or derived natural antibodies or binders may not be effective or specific as the diversity of such natural antibodies may be limited depending on the frequency or intensity of exposure to such antigens or neoepitopes.

In one approach to solve such problem, recombinant phage display libraries can be used. While such approach allows generation of libraries with reasonably high diversity, many rounds of enrichment for binders are often required, which is labor intensive and time consuming. Moreover, despite the relatively large diversity, the binders tend to have less than ideal affinities and stability. Still further, diversity is typically limited by practical considerations such as library volume, transfection efficiency, etc. Such and other approaches can be further optimized, for example, using multiple artificial selection pressures as is described in WO 2006/072773. While such methods may improve stability characteristics, significant amounts of library manipulation and time are required.

In yet another approach, mRNA display may be performed. Here, mRNA sequences encoding candidate binding molecules (typically scFv) are coupled with a puromycin molecule at their 3'-end, and peptides encoded by the mRNA sequences are generated via in vitro translation to produce a fusion product that coupled the mRNA directly to the protein encoded by the mRNA. However, while current mRNA display technology advantageously avoids problems associated with transfection limits and at least conceptually allows for higher diversity, problems with structural integrity or stability, relatively low affinity, and/or cross-reactivity still remain. To further improve at least selected binding characteristics of scFv from mRNA display, $V_H$-CDR3 spectratyping analysis was performed (see *Protein Engineering, Design & Selection,* 2015, vol. 28 no. 10, pp. 427-435). However, such process required iterative analysis and may not be productive for all antigens.

Thus, even though methods of creating and identification candidate binders using mRNA display and other methods are known, high diversity libraries with binders having high structural integrity/stability, low affinity, and/or low cross-reactivity have remained elusive. Therefore, there is still a need for improved compositions, methods for and uses of mRNA display libraries for rapid generation of stable recombinant high-affinity binders.

SUMMARY OF THE INVENTION

The inventive subject matter is directed to various compositions of, methods for, and use of a high-diversity nucleic acid library that encodes a plurality of antibodies or antibody fragments to allows for reliable and efficient identification of stable, soluble, and functional antibodies or binders to various biomolecules, and especially cancer antigens or neoepitope. Thus, one aspect of the subject matter includes a method of generating a high-diversity nucleic acid library that encodes a plurality of antibodies or antibody fragments. In this method, three sub-libraries: (1) a $V_H$-CDR1/2 sub-library, (2) a plurality of $V_H$-CDR3 sub-libraries, and (3) a $V_L$ sub-library, each having a plurality of members are generated or provided. Each member of the three sub-libraries comprises at least one random cassette that has a plurality of degenerate base positions. At least portions of at least two members of the three libraries are recombined to form an expression library member in an expression library, which has a plurality of expression library members. Each expression library member encoding a distinct antibody or antibody fragment. In a preferred embodiment, the expression library member is transcribed into an mRNA fragment, which then is coupled with a puromycin molecule at 3'-end.

In another aspect of the inventive subject matter, the inventors contemplate a composition having a plurality of nucleic acid libraries. The plurality of nucleic acid libraries includes (1) a $V_H$-CDR1/2 sub-library, (2) a plurality of $V_H$-CDR3 sub-libraries, and (3) a $V_L$ sub-library. Each of the sub-libraries (1)-(3) comprises a plurality of members and the each member of the sub-libraries comprises at least one random cassette that has a plurality of degenerate base positions.

In still another aspect of the inventive subject matter, the inventors contemplate use of the composition above for generating a high-diversity nucleic acid library.

In still another aspect of the inventive subject matter, the inventors contemplate a high-diversity nucleic acid library composition having a plurality of library members. The high-diversity nucleic acid library member includes a recombinant nucleic acid comprising a plurality of random cassettes, each having a plurality of degenerate base positions. The plurality of random cassettes is derived from at least two members from any of two libraries from the following: (1) a $V_H$-CDR1/2 sub-library, (2) a plurality of $V_H$-CDR3 sub-libraries, and (3) a $V_L$ sub-library.

In still another aspect of the inventive subject matter, the inventors contemplate use of the high-diversity nucleic acid library for generating a therapeutic recombinant antibody against a cancer neoepitope.

In still another aspect of the inventive subject matter, the inventors contemplate a method of generating a recombinant antibody. In this method, three sub-libraries: (1) a $V_H$-CDR1/2 sub-library, (2) a plurality of $V_H$-CDR3 sub-libraries, and (3) a $V_L$ sub-library, each having a plurality of members are generated or provided. Each member of the three sub-libraries comprises at least one random cassette that has a plurality of degenerate base positions. At least portions of at least two members of the three libraries are recombined to form an expression library member in an expression library, which has a plurality of expression library members. Each expression library member encoding a distinct antibody or antibody fragment. Then, the method continues with generating the recombinant antibody or fragment thereof using the expression library member.

In still another aspect of the inventive subject matter, the inventors contemplate a method of isolating a high affinity binder having an affinity of equal or less than 100 nM to an antigen, by contacting the antigen to a composition constructed by the methods described above.

In still another aspect of the inventive subject matter, the inventors contemplates a recombinant nucleic acid fragment generated using an oligonucleotide selected from Table 1 or Table 2 provided below.

In still another aspect of the inventive subject matter, the inventors contemplate a synthetic nucleic acid mixture having a nucleic acid sequence selected from Table 1 or Table 2 provided below.

Various objects, features, aspects and advantages of the inventive subject matter will become more apparent from the following detailed description of preferred embodiments, along with the accompanying drawing.

BRIEF DESCRIPTION OF THE DRAWING

FIG. 2 illustrates exemplary locations for sequence randomization in heavy chain CDR1 and CDR2.

FIG. 4 illustrates exemplary sequence randomization in light chain CDR3 with nucleic acid sequences to the left and amino acid choices to the right.

FIG. 10 shows graphs indicating binding affinities of $\alpha$B7-H4 scFv and $\alpha$B7-H4 IgG1.

DETAILED DESCRIPTION

Figure 1:
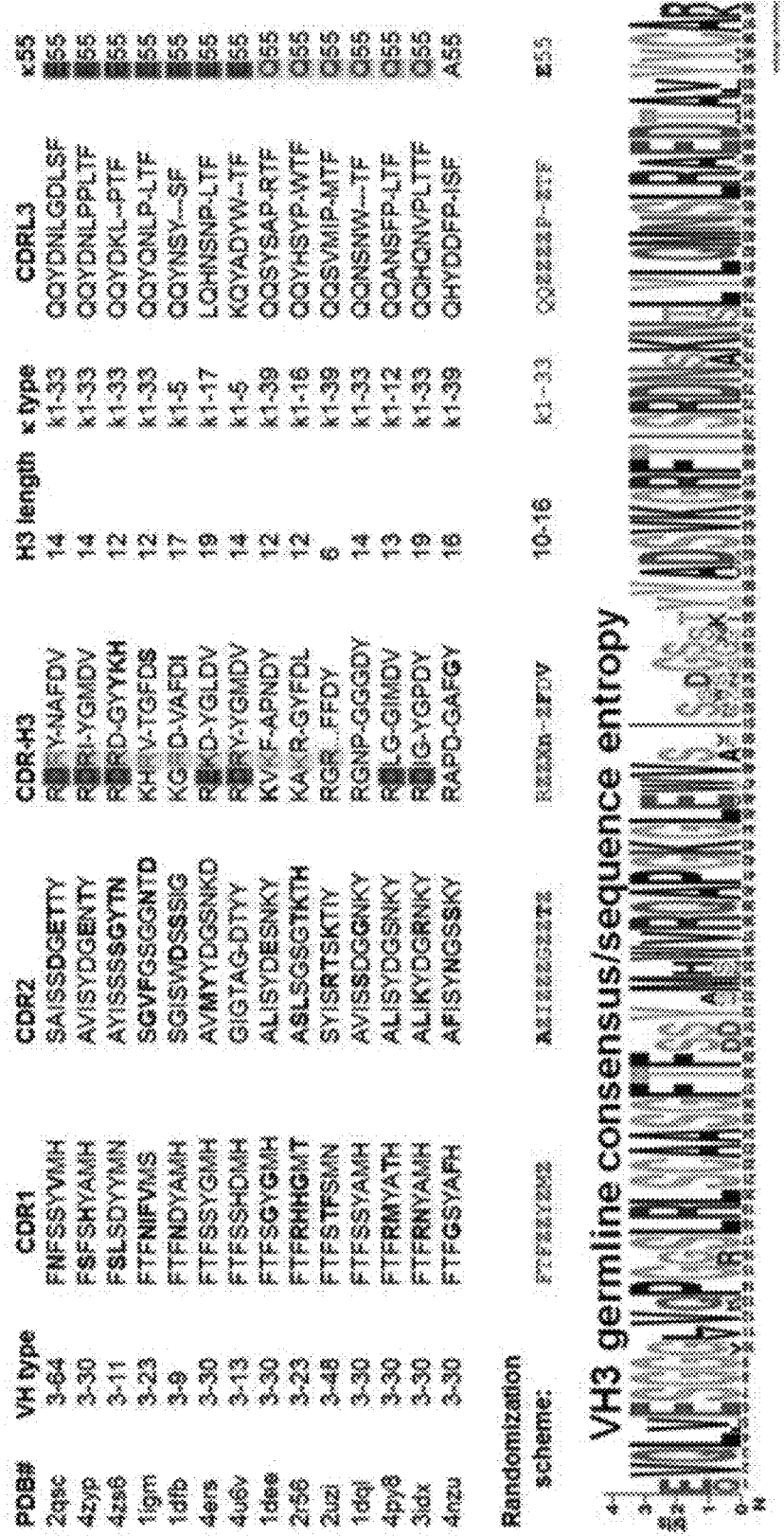
FIG. 1 illustrates one exemplary randomization strategy using VH3/Vk1 pairs.

The inventors now discovered that specific and effective recombinant antibodies or fragments thereof can be generated or identified by constructing a high-diversity nucleic acid library using targeted diversification of selected domains of the antibodies or fragments thereof encoded by members of the high-diversity nucleic acid library. In order to achieve such goal, the inventors have now discovered that one or more domains or subdomains of antibody/binder can be pre-selected and a plurality of nucleic acid sub-libraries can be generated using random cassettes in a pre-selected domain or subdomain. The inventors further discovered that the members of the sub-libraries can be recombined to construct the high-diversity nucleic acid library that allows high diversity among library members, yet provides higher probabilities of identifying antibodies/binders that are stable, soluble, functional, and adaptable when used in vivo against the cancer antigens or neoepitopes (preferably cancer-specific, patient-specific neoepitopes or neoantigens).

Indeed, and as shown in more detail below, the libraries presented herein allow for isolation of at least one binder to any arbitrary antigen, typically in a single or two-pass enrichment, where the binder has a $K_d$ of equal or less than 100 nM, and more typically equal or less than 10. Moreover, contemplated systems and methods allow for scFv libraries having a diversity of at least $10^9$, at least $10^{10}$, at least $10^{11}$, at least $10^{12}$, at least $10^{13}$, at least $10^{14}$, at least $10^{15}$, or at least $10^{16}$ distinct library members, all in a time frame that is significantly reduced as compared to conventional library construction. Thus, it should be appreciated that the speed of antibody discovery is substantially increased.

As used herein, the term "tumor" refers to, and is interchangeably used with one or more cancer cells, cancer tissues, malignant tumor cells, or malignant tumor tissue, that can be placed or found in one or more anatomical locations in a human body.

As used herein, the term "bind" refers to, and can be interchangeably used with a term "recognize" and/or "detect", an interaction between two molecules with a high affinity with a $K_D$ of equal or less than $10^{-6}$M, or equal or less than $10^{-7}$M.

As used herein, the term "provide" or "providing" refers to and includes any acts of manufacturing, generating, placing, enabling to use, or making ready to use.

Construction of Nucleic Acid Sub-Libraries

Generally, structural components (heavy chain, light chain, constant domains, variable domains) of antibodies are closely related to their functions. For example, the variable domains in the heavy chain ($V_H$) and light chain ($V_L$) constitute, together, the epitope binding domain, which provides specificity to the antibodies. Each of the $V_H$ and $V_L$ includes three complementarity determining regions (CDRs, CDR1-3) with unique amino acid sequences based on their specificity to an antigen. Thus, it had previously been contemplated that a recombinant nucleic acid library for generating or identifying antibodies can be created by randomizing the sequences encoding the CDRs of $V_H$ and $V_L$. However, the inventors found that while complete randomization of all CDRs of $V_H$ and $V_L$ may provide great diversity to the library, it also creates inefficiency in generating all combinations of random sequences and screening all randomized combinations as not all randomized $V_H$ and $V_L$ can be soluble or stably expressed when it is recombined to form an antibody (e.g., IgG1, etc.). Moreover, covering the entire diversity space is not practical due to the extremely large number of possible library members.

Thus, the inventors contemplate that subdomains of $V_H$ and $V_L$ can be divided into two categories: a framework region that are generally common among $V_H$ or $V_L$ of different antibodies (or genes encoding the antibodies) and a targeted diversification region that can be at least partially or completely randomized without significantly affecting the stability and/or solubility of the final peptide product (e.g., scFv, IgG1, etc.). Preferably, the targeted diversification region of $V_H$ includes at least a portion of CDR1, CDR2-n (N-terminus side of CDR2), CDR2-c (C-terminus side of CDR2), and CDR3. In further preferred aspects, the targeted diversification region of $V_L$ includes at least a portion of CDR3.

As such, in one exemplary and especially preferred aspect of the inventive subject matter, a nucleic acid library can be created by generating recombinant nucleic acids that include one or more random sequence cassettes in one or more targeted diversification region of $V_H$ and/or $V_L$. In one preferred embodiment, the inventors contemplate three different sub-libraries having different sets of random sequence cassettes in different targeted diversification regions such that each sub-library retains the diversity within randomized targeted diversification regions while avoiding too many randomized recombinant sequences in a single sub-library that may render the volume of the single sub-library impractical or inefficient to handle for quick or timely screenings. Furthermore, conserved areas between the targeted diversification regions are selected or designed for maximum stability and solubility.

In one embodiment, the sub-libraries include a $V_H$-CDR1/2 sub-library. The $V_H$-CDR1/2 sub-library comprises a plurality of recombinant nucleic acids (e.g., recombinant DNA) having one or more random sequence cassettes corresponding to at least a portion of $V_H$ CDR1 and/or at a portion of $V_H$ CDR2. As used herein, the random cassette corresponding to a portion of $V_H$ CDR1 means that the random cassette is located in an area of the recombinant nucleic acid, in which sequences encoding CDR1 portion should be present in order to encode a portion of $V_H$ domain which is at least structurally or functionally similar to $V_H$ domains of natural antibodies. For example, recombinant nucleic acids in a $V_H$-CDR1/2 sub-library may have a structure as below (randomized region is underlined, and fixed sequenced region is parenthesized):

5'-(Promoter-5'UTR–FW1)+<u>CDR1</u>+(FW2)+<u>CDR2</u>+
(FW3–CDR3–FW4)

As used herein, UTR refers to untranslated region and FW refers framework region (e.g., FW1 is the first framework region that may be distinct from the second framework region (FW2)). In this structure, the random sequence cassettes can be inserted in areas of CDR1 or CDR2, or preferably, both CDR1 and CDR2. In some embodiments, more than one random sequence cassettes, preferably two random sequence cassettes can be inserted in the area of CDR2: CDR2-n (for 5'-end side of CDR2) and CDR-c (for 3'-end side of CDR2).

The sub-libraries can also include a plurality of $V_H$-CDR3 sub-libraries. Each of $V_H$-CDR3 sub-library comprises a plurality of recombinant nucleic acids (e.g., recombinant DNA) having one or more random sequence cassettes corresponding to at least a portion of $V_H$ CDR3. Similar to the $V_H$-CDR1/2 sub-library, a recombinant nucleic acids in $V_H$-CDR1/2 sub-library may have a structure as below (randomized region is underlined, and fixed sequenced region is parenthesized):

5'-(Promoter-5'UTR–FW1+CDR1+FW2+CDR2+
FW3)–<u>CDR3</u>–(FW4)

Preferably, the fixed sequences (e.g., Promoter-5'UTR–FW1+CDR1+FW2+CDR2+FW3, FW4) of the recombinant nucleic acids of the $V_H$-CDR1/2 sub-library and/or the $V_H$-CDR3 sub-library are selected to use the most common and/or conserved sequences among the natural antibodies (e.g., IgG1s against various antigens) such that the fixed sequences are most expressable and adaptable to multiple formats including peptides expressed as a single chain variable fragment (scFv), a modified form of scFv, full length immunoglobulin, or a portion of immunoglobulin. Thus, in preferred embodiments, the fixed sequences of the recombinant nucleic acids of $V_H$-CDR1/2 sub-library and of the recombinant nucleic acids of $V_H$-CDR3 sub-library are at least 70%, preferably at least 80%, more preferably at least 90% identical (shared) with each other.

The sub-libraries can also include a $V_L$ sub-library. The $V_L$ sub-library comprises a plurality of recombinant nucleic acids (e.g., recombinant DNA) having one or more random sequence cassettes corresponding to at least a portion of $V_L$ CDR3. Similar to the $V_H$-CDR1/2 sub-library, recombinant nucleic acids in $V_H$-CDR1/2 sub-library may have a structure as below (randomized region is underlined, and fixed sequenced region is parenthesized):

5'-(Promoter-5'UTR–FW1+CDR1+FW2+CDR2+
FW3)–<u>CDR3</u>–(FW4)

Preferably, the fixed sequences of the recombinant nucleic acids of the $V_L$ sub-library are at least 70%, preferably at least 80%, more preferably at least 90% identical (shared) to those of recombinant nucleic acids of the $V_H$-CDR1/2 sub-library or $V_H$-CDR3 sub-library.

While any randomized sequences can be considered to generate the random sequence cassettes, the inventors contemplate that strategized random sequence cassettes for CDR1, CDR2, CDR3 of the $V_H$ and CDR3 of the $V_L$ domain would render a high complexity and large potential binding surface when expressed as a binding peptide (e.g., scFv, etc.). For example, the strategized random sequence cassettes for CDR1, CDR2 of the $V_H$-CDR1/2 sub-library may be semi-random sequence cassettes having 3 or less, preferably 2 or less, or more preferably, one random sequence (encoding 3 or less, 2 or less, or one random amino acid per cassette) per cassette. The location of the random sequence in the random cassette may vary depending on the random amino acid in the cassette. In another example, the strategized random sequence cassettes for CDR3 of $V_H$-CDR3 sub-library may include more randomized sequences such that 4 or more, preferably 5 or more, or more preferably 6 or more random sequences (encoding 4 or more, preferably 5 or more, or more preferably 6 or more random amino acids per cassette) are present per cassette. In yet another example, the strategized random sequence cassettes for CDR3 of V_L sub-library may include more randomized sequences such that 4 or more, preferably 5 or more, or more preferably 6 or more random sequences (encoding 4 or more, preferably 5 or more, or more preferably 6 or more random amino acid per cassette) are present per cassette.

In an especially preferred aspect of the inventive subject matter, the inventors contemplate that preferred random sequence cassettes for sub-libraries can be generated using oligonucleotides presented in Table 1 (for $V_H$-CDR1/2 sub-library and $V_H$-CDR3 sub-library), and Table 2 (for $V_L$ sub-library). As shown in Tables 1 and 2, each oligonucleotide includes a random sequences (highlighted) having degenerate code, shown as IUPAC ambiguity codes. For example, one oligonucleotide for CDR1 random sequence cassette includes a random sequence "RVT", which represents "A/G,A/C/G,T", whose combination can encode one of threonine (T), alanine (A), asparagine (N), aspartic acid (D), serine (S) or glycine (G). The choice of amino acids encoded by the degenerate codons are depicted to the right and are indicated with X.

Additionally and preferably, the random sequence cassettes for $V_H$-CDR3 sub-library may include nucleic acid sequences in different length. For example, the random sequence cassettes for $V_H$-CDR3 sub-library may be in any length between 10-30 amino acids, preferably between 10-25 amino acids, more preferably between 10-20 amino acids. Thus, as shown in Table 1, the oligonucleotides for generating random sequence cassette for $V_H$-CDR3 sub-library may include a various repeats (e.g., 4-10 repeats) of "NNK" (which represents G/A/T/C, G/A/T/C, G/T) between sequences encoding D/G-R/L and A/G (see also FIG. 3). Generation and diversity of light chain sequences are exemplarily shown in FIG. 4.

TABLE 1

| | | |
|---|---|---|
| $V_H$ CDR1 | SEQ ID NO. 1:<br>GGCTTAGGTCTCATTTCRVTAGTTACGCTATGCATTGGGCGAGACGAGGTCTGAACGG | X = T, A, N, D, S, G |
| | SEQ ID NO. 2:<br>GGCTTAGGTCTCATTTCTCTRVKTACGCTATGCATTGGGCGAGACGAGGTCTGAACGG | X = T, A, N, K, D, E, S, R, G |
| | SEQ ID NO. 3:<br>GGCTTAGGTCTCATTTCTCTAGTTACKKGATGCATTGGGCGAGACGAGGTCTGAACGG | X = G, W, L, V |
| | SEQ ID NO. 4:<br>GGCTTAGGTCTCATTTCTCTAGTTACWMTATGCATTGGGCGAGACGAGGTCTGAACGG | X = S, Y, T, N |
| | SEQ ID NO. 5:<br>GGCTTAGGTCTCATTTCTCTAGTTACGCTATGAVTTGGGCGAGACGAGGTCTGAACGG | X = S, T, N |
| $V_H$ CDR2-n | SEQ ID NO. 6:<br>GGCTTAGGTCTCGTTCATHCATTAGTGGTAGTGGACGAGACGAGGTCTGAACGG | X = Y, F, S |
| | SEQ ID NO. 7:<br>GGCTTAGGTCTCGTTCAVKTATTAGTGGTAGTGGACGAGACGAGGTCTGAACGG | X = V, G, I, S, L, R |
| | SEQ ID NO. 8:<br>GGCTTAGGTCTCGTTCAGCTATTYGGGGTAGTGGACGAGACGAGGTCTGAACGG | X = W, R |
| | SEQ ID NO. 9:<br>GGCTTAGGTCTCGTTCAGCTATTDATGGTAATGGACGAGACGAGGTCTGAACGG | X = Y, N, D + N53 |
| | SEQ ID NO. 101:<br>GGCTTAGGTCTCGTTCAGCTATTAGTWMTAGTGGACGAGACGAGGTCTGAACGG | X = Y, S, T, N |
| | SEQ ID NO. 11:<br>GGCTTAGGTCTCGTTCAGCTATTAGTKGGAGTGGACGAGACGAGGTCTGAACGG | X = W, G |
| | SEQ ID NO. 12:<br>GGCTTAGGTCTCGTTCAGCTATTAGTGGTRRTGGACGAGACGAGGTCTGAACGG | X = D, G, S, N |
| $V_H$ CDR2-c | SEQ ID NO. 13:<br>GGCTTAGGTCTCGTGGARVKAGTACTTACTACGCGAGACGAGGTCTGAACGG | X = S, T, G, A, N, K, D, E |
| | SEQ ID NO. 14:<br>GGCTTAGGTCTCGTGGAGGTNATACTTACTACGCGAGACGAGGTCTGAACGG | X = Y, N, D, H |
| | SEQ ID NO. 15:<br>GGCTTAGGTCTCGTGGAGGTRVAACTTACTACGCGAGACGAGGTCTGAACGG | X = T, K, R, E, A, G |
| | SEQ ID NO. 16:<br>GGCTTAGGTCTCGTGGAGGTAGTACTVRTTACGCGAGACGAGGTCTGAACGG | X = D, G, N, S, H, R |
| VH CDR3 | SEQ ID NO. 17:<br>GGCTTAGGTCTCTCCGTGRTCKC(NNK)nGSTTTCGCGAGACGAGGTCTGAACGG | (D, G)-(R, L)-<br>(Xaa = 4-10)-(A, G) |

TABLE 2

| | | |
|---|---|---|
| $V_L$ CDR3 | SEQ ID NO. 18:<br>GGCTTAGGTCTCTGCAGDSGDMTRVTDSGCCTTWCACTTCGAGACGAGGTCTGAACGG | Q-$X_1$-$X_2$-$X_3$-$X_4$-P-$X_5$<br>$X_1$ = Y, D, L, A, H, S, |
| | SEQ ID NO. 19:<br>GGCTTAGGTCTCTGCAGBWTDMTRVTDSGCCTTWCACTTCGAGACGAGGTCTGAACGG | F, R, T, W, G<br>$X_2$ = Y, N, D, S, T, A |
| | SEQ ID NO. 20:<br>GGCTTAGGTCTCTGCAGDSGDMTRVTNWTCCTTWCACTTCGAGACGAGGTCTGAACGG | $X_3$ = S, N, T, A, D, G<br>$X_4$ = Y, F, A, L, T, S, |
| | SEQ ID NO. 21:<br>GGCTTAGGTCTCTGCAGBWTDMTRVTNWTCCTTWCACTTCGAGACGAGGTCTGAACGG | H, W, I, N, R, V, D, G<br>$X_5$ = L, Y, W, F, R |
| | SEQ ID NO. 22:<br>GGCTTAGGTCTCTGCAGDSGDMTRVTDSGCCTYKGACTTCGAGACGAGGTCTGAACGG | |
| | SEQ ID NO. 23:<br>GGCTTAGGTCTCTGCAGBWTDMTRVTDSGCCTYKGACTTCGAGACGAGGTCTGAACGG | |
| | SEQ ID NO. 24: | |

TABLE 2-continued

```
GGCTTAGGTCTCTGCAGDSGDMTRVTNWTCCTYKGACTTCGAGACGAGGTCTGAACGG
SEQ ID NO. 25:
GGCTTAGGTCTCTGCAGBWTDMTRVTNWTCCTYKGACTTCGAGACGAGGTCTGAACGG
```

Most typically, the oligonucleotides presented in Table 1 and 2 are provided in a single strand DNA, which can be converted using DNA polymerase I (Klenow fragment) into double-stranded DNA fragment to so be inserted into a backbone comprising the fixed sequenced region (e.g., 5'-(Promoter-5'UTR–FW1+CDR1+FW2+CDR2+FW3)–(FW4) for recombinant nucleic acids of $V_L$ sub-library, etc.). Yet, it is also contemplated that the oligonucleotides presented in Table 1 and 2 are also present with the complementary oligonucleotides to form a double stranded nucleic acids without using polymerase enzymes.

In some embodiments, the recombinant nucleic acids of sub-libraries also include a nucleic acid sequence encoding a protein tag such that the peptide encoded by the recombinant nucleic acids can be isolated using the binder against the protein tag. For example, preferred proteins tag include a FLAG tag (with a sequence motif DYKDDDDK), a Myc tag (with a sequence motif EQKLISEEDL), and an HA-tag. In some embodiments, the protein tags can be repeated to strengthen the signal or increase the detection (e.g., three repetitions of FLAG tag (3×FLAG), etc.)

It is contemplated that some random sequence cassettes inserted in the recombinant nucleic acids of sub-libraries, may introduce frame shifts, nonsense mutations, and sequence(s) that are destabilizing the structure of the peptide encoded by the recombinant nucleic acids. Thus, in some embodiments, the inventors contemplate that the recombinant nucleic acids of sub-libraries are in vitro tested so that any recombinant nucleic acids encoding unstable or misfolded peptides can be removed from the library. For example, the recombinant nucleic acids of the $V_H$-CDR3 sub-libraries or the $V_L$ sub-library can be tested for their binding affinity to protein A of Staphylococcus aureus or protein L of Finegoldia magna, which binds to structured epitopes of $V_H3$ domain or $V_L$ (Vκ) domain of immunoglobulin independently to CDR sequences, respectively.

Any suitable methods to screen the recombinant nucleic acids by their binding affinities to protein A or protein L are contemplated. In one exemplary embodiment the recombinant nucleic acids of sub-libraries are transcribed into mRNAs by in vitro transcription and the 3'-end of the mRNAs are coupled (covalently linked) to puromycin. The puromycin-coupled mRNAs are in vitro translated such that the peptides transcribed from the puromycin-coupled mRNAs are coupled with the mRNAs via the puromycin. Next, the peptides are contacted with protein A or protein L to identify peptides effectively binding to the protein A or protein L. Preferably, peptides binding to the protein A or protein L with an affinity with a $K_D$ of equal or less than $10^{-6}$M, preferably equal or less than $10^{-7}$M are selected and isolated. Once the peptides with high affinity to protein A or protein L are isolated, cDNAs of the isolated peptides can be generated via in vitro reverse-transcription of the mRNAs coupled with the puromycin and the peptides. The so generated cDNAs of the isolated peptides can be then inserted as random sequence cassettes to generate selected recombinant nucleic acids of $V_H$-CDR3 sub-libraries or the $V_L$ sub-library. Alternatively, it is also contemplated that the recombinant nucleic acids of sub-libraries can be present in a form of mRNAs, which is optionally pre-coupled with puromycin molecule such that the in vitro transcription step for the recombinant nucleic acids (in DNA format) may not be needed.

Construction of scFv Library from the Sub-Libraries

The inventors further contemplate that at least two recombinant nucleic acids (members) of the sub-libraries can be recombined to form recombinant scFv nucleic acids. In a preferred embodiment, each of the at least two recombinant nucleic acids (members) is selected from different sub-libraries. For example, one recombinant nucleic acid may be selected from each of the $V_H$-CDR1/2 sub-library, the plurality of $V_H$-CDR3 sub-libraries, and the $V_L$ sub-library. For other example, one recombinant nucleic acid may be selected from each of two of $V_H$-CDR1/2 sub-library, the plurality of $V_H$-CDR3 sub-libraries, and the $V_L$ sub-library. Preferably, at least one of, more preferably all of, the recombinant nucleic acid(s) selected from the sub-libraries are pre-selected via affinity binding screening as described above.

Most typically, the recombinant scFv nucleic acids can be constructed by recombining a portion of the recombinant nucleic acids from sub-libraries. In this embodiment, the portion of the recombinant nucleic acids includes the random sequence cassettes inserted into the recombinant nucleic acids. Thus, for example, as a first step, the portion of the recombinant nucleic acids of the $V_H$-CDR1/2 sub-library can be 5'-[CDR1+(FW2)+CDR2]-3' (random sequence cassettes are underlined), preferably 5'-(portion of FW1)-[CDR1+(FW2)+CDR2]-(portion of FW3)-3', more preferably 5'-(Promoter-5'UTR–FW1)+CDR1+(FW2)+CDR2+(portion of FW3)-3' or 5'-(Promoter-5'UTR–FW1)+CDR1+(FW2)+CDR2+(a small linker)-3'. Similarly, for example, the portion of the recombinant nucleic acids of the $V_H$-CDR3 sub-libraries can be 5'-[CDR3]-3' (random sequence cassettes are underlined), preferably 5'-(portion of FW3)-CDR3-(portion of FW4)-3', more preferably, 5'-(portion of FW3)-CDR3-(FW4)-3', or 5'-(a small linker)-CDR3-(FW4)-3'. The portions of the recombinant nucleic acids from the $V_H$-CDR1/2 sub-library and the $V_H$-CDR3 sub-libraries are then isolated (e.g., by PCR) and can be recombined (e.g., fused via restriction-ligation methods, generated via a recombinant-PCR, etc.) to form a $V_H$ domain recombinant nucleic acid. Thus, typically, the $V_H$ domain recombinant nucleic acid would be in a structure of 5'-Promoter-5'UTR–FW1+CDR1+FW2+CDR2+FW3–CDR3–FW4-3'(random sequence cassettes are underlined). Optionally, the $V_H$ domain recombinant nucleic acid may also include a nucleic acid sequence encoding a protein tag (e.g., FLAG tag, Myc tag, HA tag, etc.) in its 3'-end as described above. In addition, such generated $V_H$ domain recombinant nucleic acids can be placed in a $V_H$ domain library as $V_H$ domain library members.

Figure 5:
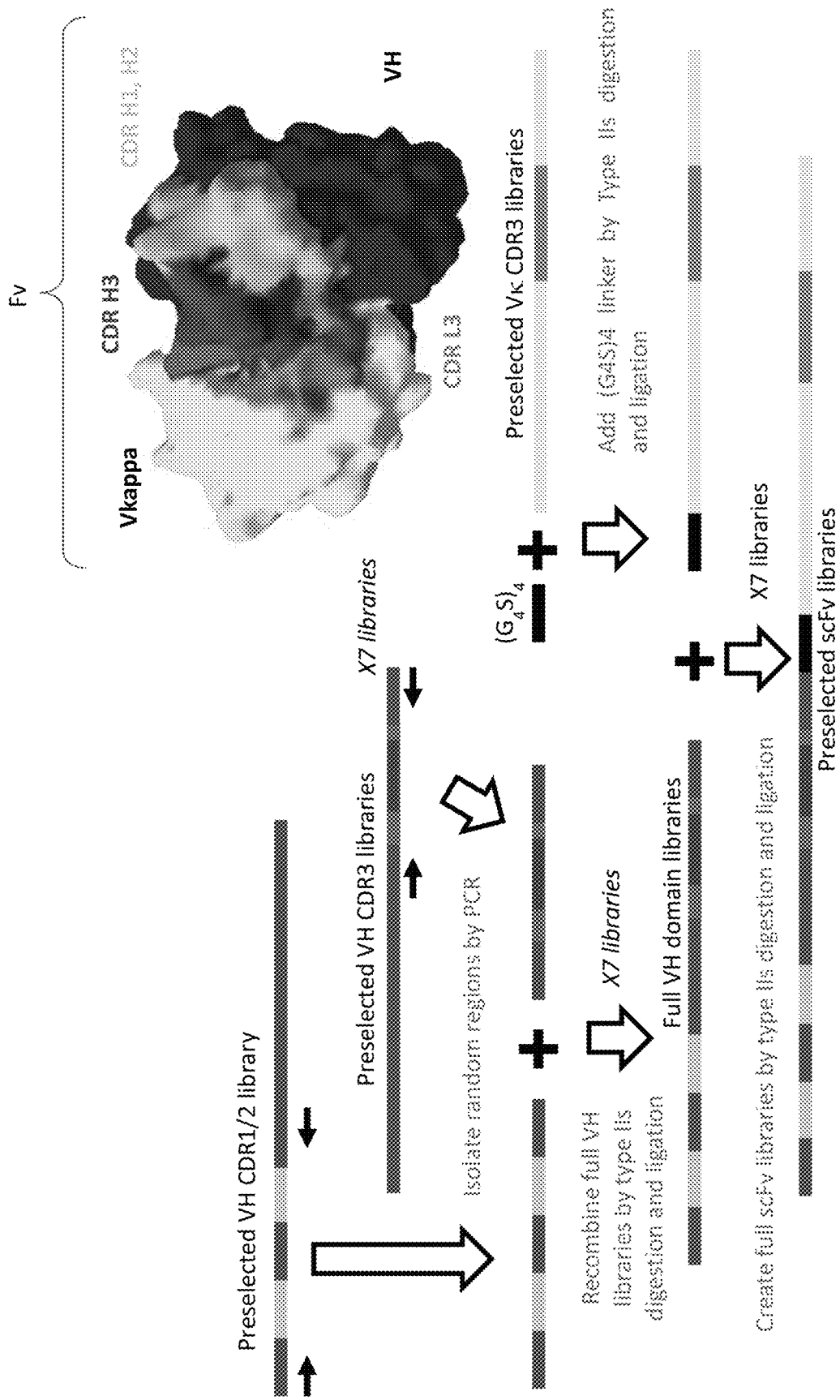
FIG. 5 illustrates an exemplary generation of hybrid nucleic acid elements by isolating and combining random cassettes of multiple recombinant nucleic acid segments.

The so formed $V_H$ domain recombinant nucleic acids can be further recombined with recombinant nucleic acids of the $V_L$ sub-library to form the recombinant scFv nucleic acids. FIG. 5 shows one exemplary method of recombining the sequences from sub-libraries. As shown, and also typically, a portion of the $V_H$ domain recombinant nucleic acid and a portion of the recombinant nucleic acid of the $V_L$ sub-library are fused into one the recombinant scFv nucleic acids. For example, the portion of $V_H$ domain recombinant nucleic acid may include 5'-Promoter-[5'UTR–FW1+CDR1+FW2+CDR2+FW3–CDR3–FW4-3' (preferably without any nucleic acid encoding a protein tag in its 3'-end), and the portion of the recombinant nucleic acid of the $V_L$ sub-library may include FW1'+CDR1+FW2'+CDR2+FW3'–CDR3–FW4' (without promoter and 5'-UTR) such that the recombinant nucleic acid of the $V_L$ sub-library can be fused to the 3'-end of the portion of $V_H$ domain recombinant nucleic acid. Thus, the typical recombinant scFv nucleic acid would be in a structure of 5'-Promoter–[5'UTR–FW1+CDR1+FW2+CDR2+FW3–CDR3–FW4]$V_H$–[FW1'+CDR1+FW2'+CDR2+FW3'–CDR3–FW4']$V_L$-3'. It is highly preferred that the portion of $V_H$ domain recombinant nucleic acid and the portion of the recombinant nucleic acid of the $V_L$ sub-library are placed in the same reading frame such that they encode a single polypeptide.

Preferably, the portion of $V_H$ domain recombinant nucleic acid and the portion of the recombinant nucleic acid of the $V_L$ sub-library are fused via a nucleic acid encoding a linker (a short peptide spacer fragment) between two portions. Any suitable length and order of peptide sequence for the linker or the spacer can be used. However, it is preferred that the length of the linker peptide is between 3-30 amino acids, preferably between 5-20 amino acids, more preferably between 5-15 amino acids. For example, the inventors contemplate that glycine-rich sequences (e.g., gly-gly-ser-gly-gly, etc.) are employed to provide flexibility of scFv between the $V_H$ and $V_L$ domains.

Optionally, the recombinant scFv nucleic acids may also include a nucleic acid sequence encoding a protein tag (e.g., FLAG tag, Myc tag, HA tag, etc.) in its 3'-end as described above. In addition, such generated recombinant scFv nucleic acids can be placed in an expression library as expression library members.

In some embodiments, the so formed recombinant scFv nucleic acids are further screened and/or ranked based on their binding affinities to one or more ligands of interest (e.g., cancer antigens, neoepitopes, etc.), stability, pH sensitivity, and/or species cross-reactivity. For example, the stability of the scFv peptides encoded by the recombinant scFv nucleic acids can be analyzed by size exclusion chromatography measuring the size of the peptide over time. For other example, pH sensitivity and binding affinity of the scFv peptides encoded by the recombinant scFv nucleic acids can be analyzed by contacting the scFv peptides with one or more ligands in different buffer conditions (pH, temperature, etc.).

For those analysis and further isolation of desired recombinant scFv nucleic acids from the expression library, the inventors contemplate that the recombinant scFv nucleic acids can be present in a form of mRNAs, which is optionally pre-coupled with puromycin molecule at the 3'-end of the mRNAs. The puromycin-coupled mRNAs can then be in vitro translated such that the peptides transcribed from the puromycin-coupled mRNAs are coupled with the mRNAs via the puromycin. Then, the peptides are contacted with one or more ligands, optionally in different buffer conditions (pH, temperature, etc.). Preferably, peptides binding to the ligand with an affinity with a $K_D$ of equal or less than $10^{-6}$M, preferably equal or less than $10^{-7}$M, between pH 5.0-8.0, preferably between pH 6.0-8.0, more preferably between pH 6.5-8.0 are selected and isolated. Once the peptides with high affinity to the ligand(s) are isolated, cDNAs of the isolated peptides can be generated via in vitro reverse-transcription of the mRNAs coupled with the puromycin and the peptides.

Additionally, the so generated cDNAs of the isolated peptides encoded by recombinant scFv nucleic acids can be grafted on and replaced the portion of the immunoglobulin to form a recombinant immunoglobulin or fragments thereof. For example, the so generated cDNA can be fused with the backbone of the immunoglobulin heavy chain constant region such that the variable region of heavy and light chain of the immunoglobulin can be replaced with the scFv formed by the isolated peptide. Alternatively, the inventors also contemplate that the $V_H$ portion (or derived from $V_H$ domain recombinant nucleic acid) and $V_L$ portion (or derived from of the recombinant scFv nucleic acid) of the recombinant scFv nucleic acids can be grafted on and replaced the portion of the immunoglobulin to form a recombinant immunoglobulin or fragments thereof. For example, the $V_H$ portion (or derived from $V_H$ domain recombinant nucleic acid) and $V_L$ portion (or derived from of the recombinant scFv nucleic acid) of the recombinant scFv nucleic acids are fused with the backbone of the immunoglobulin heavy chain constant region or light chain constant region, respectively, to form an immunoglobulin with variable regions specific to the desired ligand.

In these examples, it is contemplated that the immunoglobulin can include any type (e.g., IgG, IgE, IgM, IgD, IgA and IgY) and any class (e.g., IgG1, IgG2, IgG3, IgG4, IgA1 and IgA2) of heavy chain or constant domain to constitute different types of immunoglobulin. In addition, the "antibody" can include, but not limited to a human antibody, a humanized antibody, a chimeric antibody, a monoclonal antibody, a polyclonal antibody. In this context, it should be noted that contemplated systems and methods allow for the generation of species-specific antibodies by grafting the isolated $V_H$ and $V_L$ domains onto the remainder of the antibody of a desired species (e.g., human). In another example, the so generated cDNA can be fused with nucleic acids encoding other portion of the immunoglobulin to form a fragment of the immunoglobulin. In this example, it is contemplated that the fragment of the immunoglobulin can be Fab fragments, Fab' fragments, F(ab')2, disulfide linked Fvs (sdFvs), and Fvs. The inventors further contemplate that a portion of the so generated cDNA can be fused with nucleic acids encoding other portion of the immunoglobulin to form any fragment comprising either $V_H$ segment and/or $V_L$ segment.

Additionally, the inventors contemplate that the scFv portions may also be used as targeting entities for various proteins and non-protein molecules. For example, the scFv portions may be coupled (typically as chimeric protein) to an ALT-803 type molecule to form a TxM entity that has specific targeting capability (see e.g., *J Biol Chem.* 2016 Nov. 11; 291(46):23869-23881). In another example, the scFv portion may be coupled to a carrier protein (e.g., albumin) to allow target specific delivery of one or more drugs to a specific location in a tumor microenvironment where the drugs are coupled to the carrier.

The inventors further contemplate that by construction the sub-libraries via targeted diversification of random sequences, and/or preselecting the members of the sub-libraries, the expression library can achieve approximately $10^{12}$ complexity with minimal sacrifice of diversity by removing unstable, non-binding, or misfolded sequences. Thus, the above described approach to generate expression library provides meaningful size of sequence complexity, yet is practical to screen binders/antibodies in a small volume. In addition, the above described approach to generate expression library simplified the screening procedure of the binders/antibodies. Traditionally, in vitro validation of any nucleic acid sequences (e.g., randomized sequences) encoding binding domain (or motif) required the nucleic acid sequences converted to Fab domain, then the binding affinity could be tested via pull-down assay with the ligand of interest. The methods presented herein allows in vitro validation of nucleic acid sequences encoding binding domain (or motif) via ranking by affinity (e.g., Kd value), pH sensitivity, and species cross-reactivity (e.g., via surface plasmon resonance assay, etc.) without converting the nucleic acid sequences into Fab domain. Further, pre-selection of members from each library based on stability and sensitivity reduces the pool to be tested in the library such that the desired binders/scFv/antibody domains can be identified more quickly and efficiently. Therefore, the inventors also contemplate methods for isolation of high-affinity binders (e.g., with nano- and picomolar $K_d$) from a high-diversity pool using mRNA display techniques in which library members after in vitro translation are screened against a solid phase bound antigen. Once binders are identified, they can be further characterized by surface plasmon resonance spectroscopy with respect to affinity and $K_{on}/K_{off}$ characteristics as is further described below. Viewed form a different perspective, contemplated systems and methods allow for rapid detection of binders and generation of scFv or antibodies in a process that is entirely independent from an in vivo immune system.

Examples

While any suitable diversification scheme to identify targeted diversification region(s) can be contemplated to maximize diversity while maintaining efficiency, the inventors found that VH3/Vk1 can be one of the good candidate regions for randomization among the various domains of immunoglobulin, VH3 is considered by far most stable and soluble $V_H$ domain, and Vk1 of light chain is stable and soluble. Thus, it is contemplated that the VH3/Vk1 randomized pairs would convert to a full size immunoglobulin more efficiently. Accordingly, the inventors developed pre-selection strategy using VH3 and Vk1 frameworks. FIG. 1 shows one exemplary randomization strategy using VH3/Vk1 pairs. Protein sequences of at least 14 immunoglobulin molecules specific to one antigen are compared and analyzed. The most stable and conserved sequences among 14 immunoglobulin molecules are used as frameworks and locus of variable sequences are analyzed to use as randomized sequences and the degree of randomization (e.g., complete random, partially random, etc.).

Figure 3:
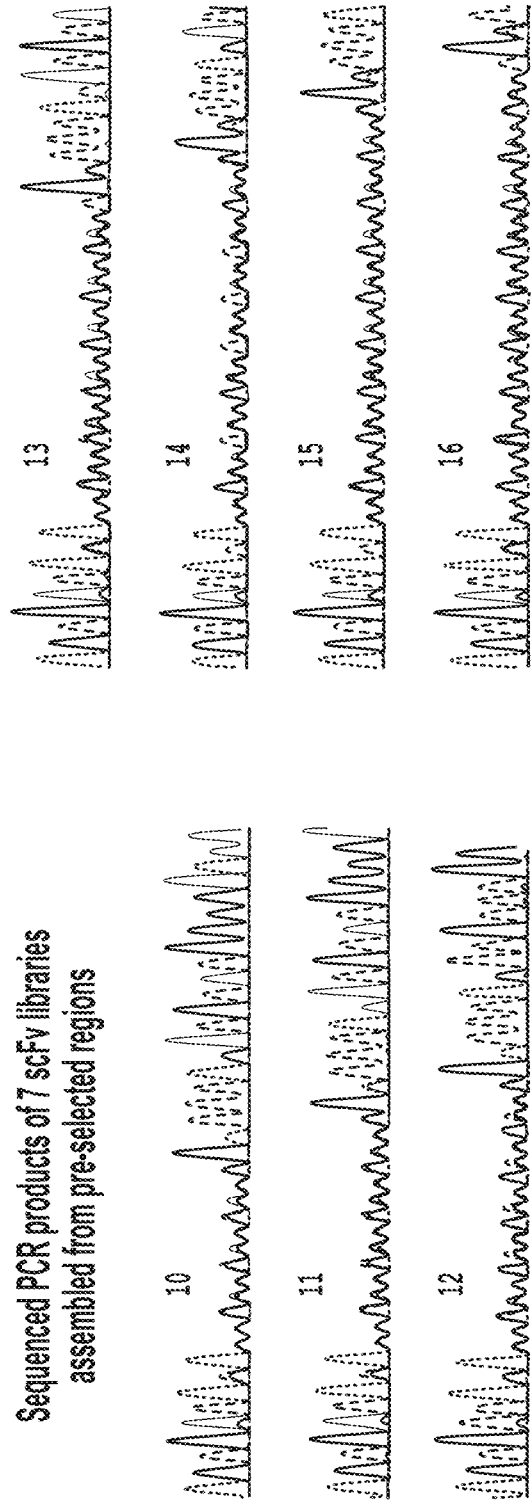
FIG. 3 illustrates exemplary sequence randomization in heavy chain CDR3.

Based on the randomization strategy, the inventors further generated targeted diversified sequences (randomized sequences, random oligos) for CDR1, CDR2-n, CDR2-c of $V_H$ domain (see FIG. 2) and for CDR3 of $V_H$ domain (see FIG. 3). The process of generating recombinant scFv nucleic acids using the random oligos of CDR1, CDR2-n, CDR2-c, CDR3 of $V_H$ domain, and CDR3 of $V_L$ domain is described above and also shown in the schematic diagram in FIG. 4. A high-diversity library was constructed as exemplarily shown in FIG. 5 and discussed in more detail above.

Figure 6:
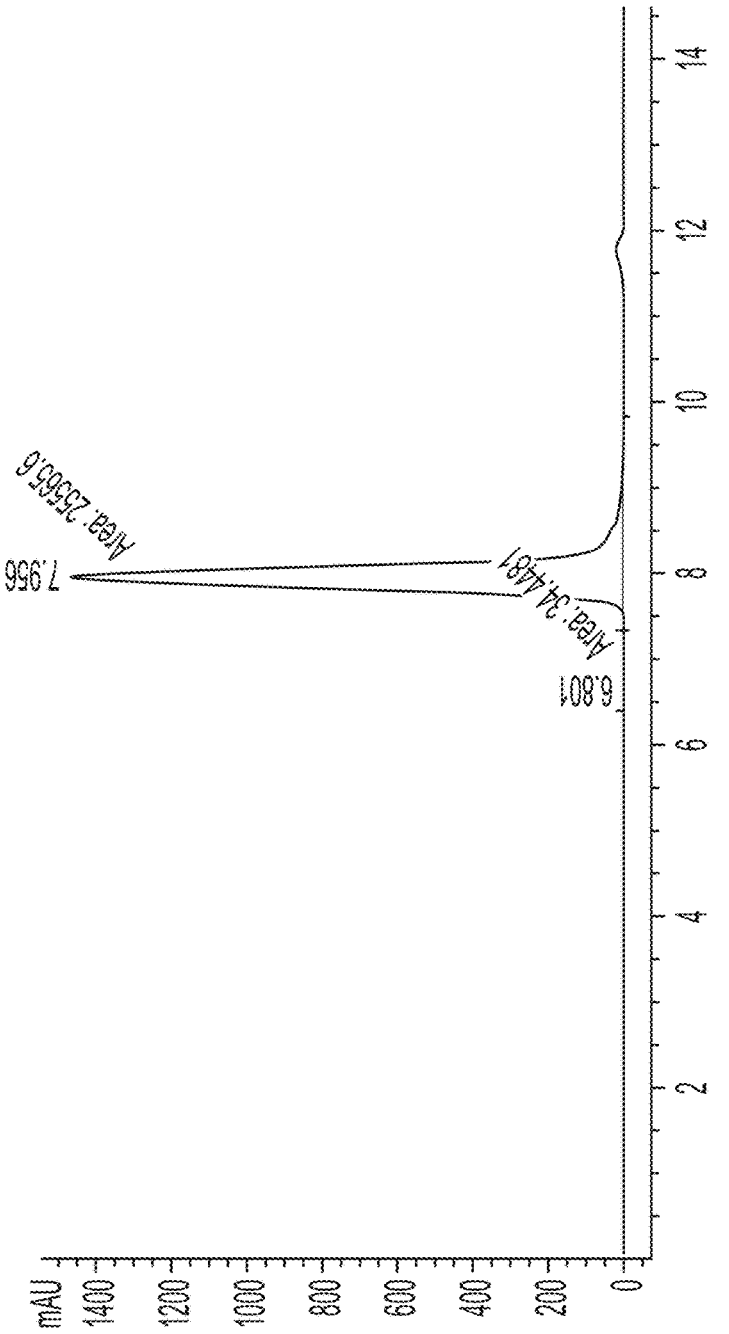
FIG. 6 shows a size exclusion chromatography result showing a single peak indicating a stable protein expression of $\alpha$B7-H4$_{801}$.

Using the targeted diversification scheme and methods of generating recombinant scFv nucleic acids as described in FIGS. 1-5, the inventors generated a high-diversity library and isolated therefrom a recombinant α-B7-H4$_{801}$ (α-B7-H4, clone number 801) binder. The stability of the recombinant α-B7-H4$_{801}$ was determined by analytical size exclusion chromatography over 15 min to evaluate any degradation or deformation of the antibody. As shown in FIG. 6, the eluate of α-B7-H4$_{801}$ shows a single peak without any significant smaller peaks, indicating the α-B7-H4$_{801}$ binder generated by methods described above could produce scFv or an antibody with high stability.

Figure 7:
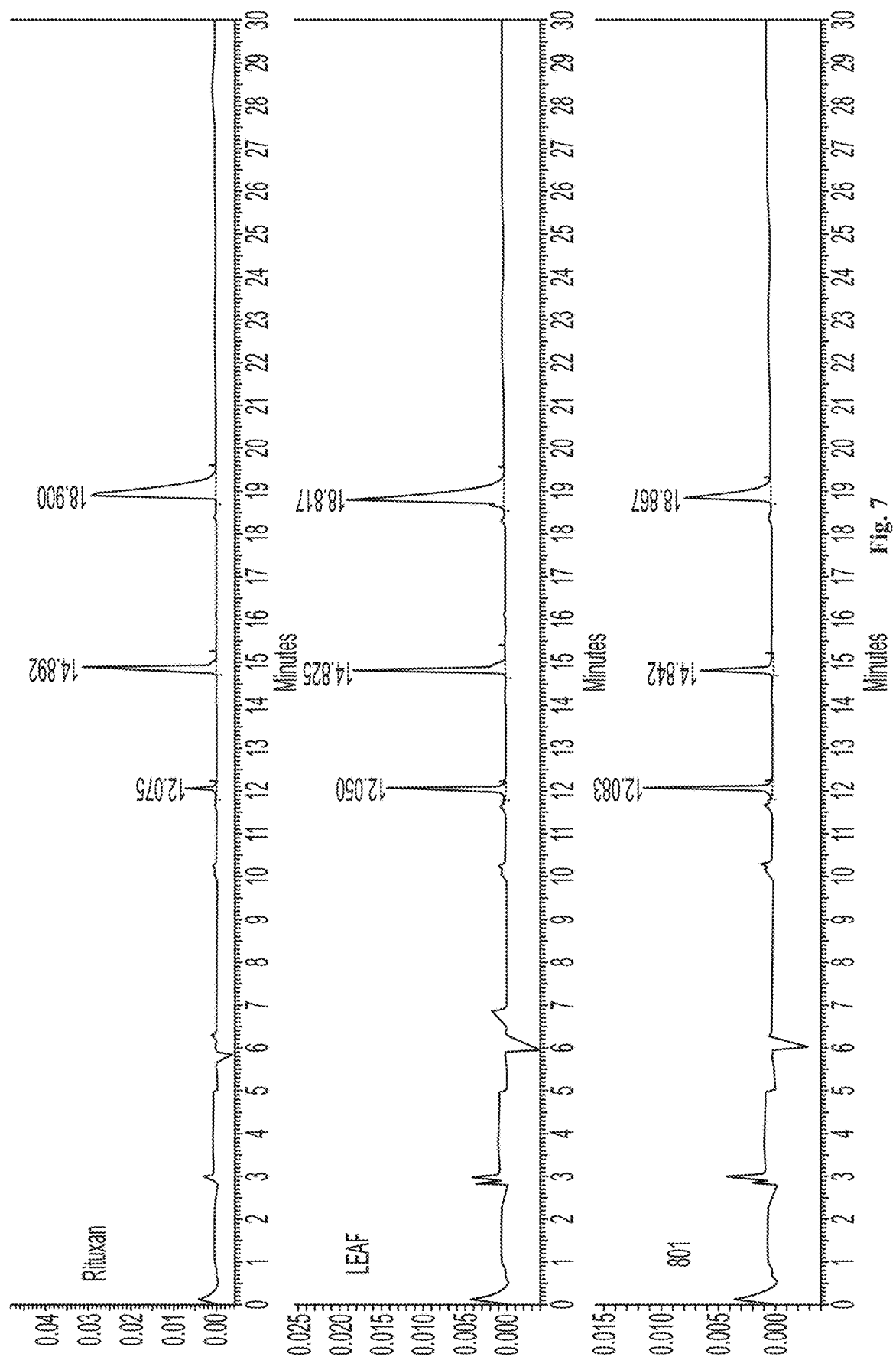
FIG. 7 shows a capillary electrophoresis sodium dodecyl sulfate (CE-SDS) data indicating similar molecular behavior of $\alpha$B7-H4$_{801}$ compared to commercial antibodies.

The inventors found that the recombinant α-B7-H4$_{801}$ comprises antibody components of substantially similar to other commercially available α-B7-H4 antibodies (Rituxan®, LEAF®). The fragments of the recombinant α-B7-H4$_{801}$ and two commercially available α-B7-H4 antibodies (Rituxan®, LEAF®) were analyzed via Capillary electrophoresis sodium dodecyl sulfate (CE-SDS). As shown in FIG. 7, CE-SDS separation of recombinant α-B7-H4$_{801}$ antibody and two commercially available α-B7-H4 antibodies (Rituxan®, LEAF®) fragments show two profound peaks, each corresponds to light chain (middle peak) and glycosylated heavy chain (right peak). Left peak indicates the location of a 10 Kd standard marker for the CE-SDS analysis.

Figure 8:
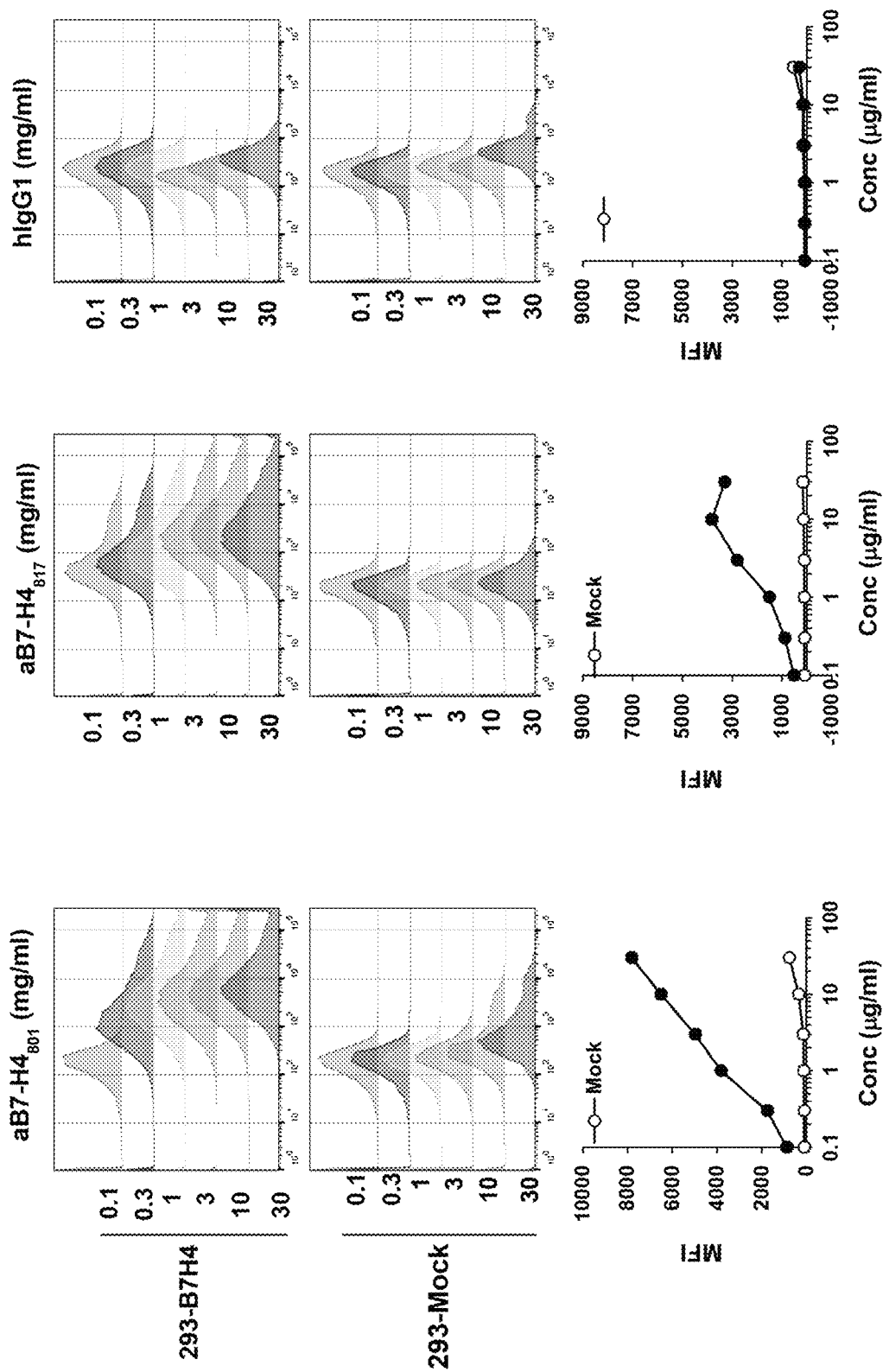
FIG. 8 shows graphs indicating binding of in vitro selected $\alpha$B7-H4 antibodies to B7-H4.

The inventors further found that various recombinant α-B7-H4 antibodies may show different binding characters (e.g., affinities, specificities, etc.) to the target ligand. FIG. 8 shows two recombinant α-B7-H4 antibodies, α-B7-H4$_{801}$ and α-B7-H4817 that are tested for binding with B7-H4 expressing 293T cells, measured by mean fluorescence intensity (MFI). The results show that α-B7-H4$_{801}$ antibodies have higher binding affinity to B7-H4 expressing 293T cells compared to α-B7-H4817 antibodies, indicating differently randomized CDR domains may render different binding affinities to the ligand. The right most panels show the control experiment with nonspecific human IgG1 (hIgG1).

Figure 9:
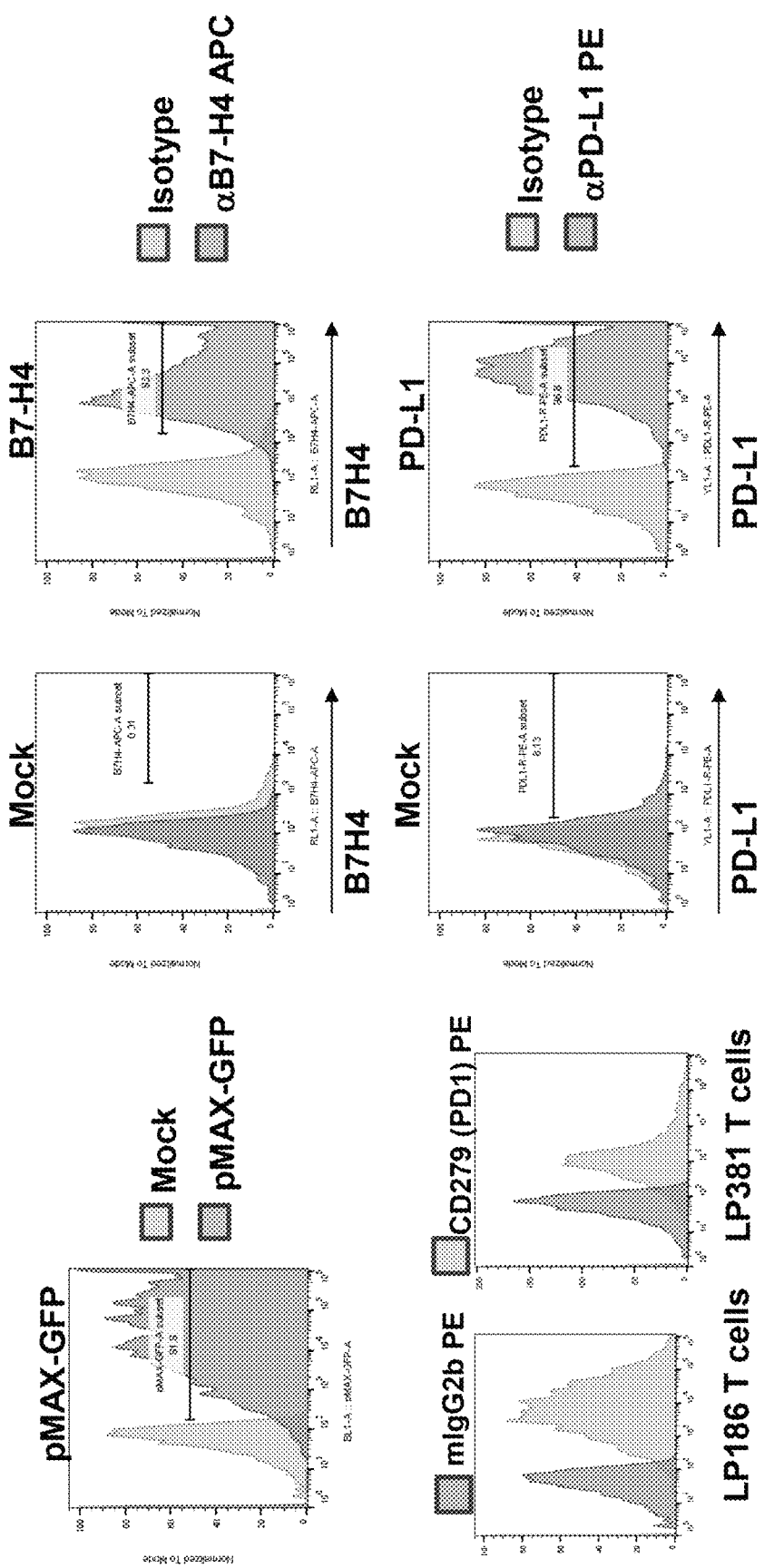
FIG. 9 shows graphs of functional analysis of in vitro selected $\alpha$B7-H4 binders and $\alpha$PD-L1 binders.

The recombinant α-B7-H4 antibodies were further tested to determine specific and effective binding to the ligands (B7-H4) expressed on the antigen presenting cells (APCs) using flow cytometry. As shown in FIG. 9, the recombinant α-B7-H4 antibodies could specifically bind to B7-H4 ligands (separating the peak out from nonspecific isotype binding), indicating that the recombinant α-B7-H4 antibodies are fully functional.

The inventors also found that scFv peptide against B7-H4 (scFv B7-H4$_{801}$) and recombinant α-B7-H4 antibodies (IgG α-B7-H4$_{801}$) generated by the same scFv peptide with the scFv B7-H4$_{801}$ are functionally compatible using the surface plasmon resonance assay. In this assay, Flag-tagged scFv B7-H4$_{801}$ are immobilized on the surface via α-Flag biotinylated antibody, which is coupled with surface-linked neutravidin. The surface immobilized scFv B7-H4$_{801}$ peptides are then contacted with analyte including B7-H4. Similar assay was performed with α-B7-H4 antibodies. As shown in FIG. 10 and Table 3, scFv B7-H4$_{801}$ and IgG α-B7-H4$_{801}$ shows substantially similar affinity and binding characteristics to B7-H4, indicating that they are functionally compatible. Further, as the binding affinity of in vitro translated peptide (scFv) can be directly measured without grafting the peptide into an antibody backbone, more recombinant scFv nucleic acids in the expression library can be screened efficiently.

TABLE 3

|  | Ka | Kd | KD | Res sd |
|---|---|---|---|---|
| IgG | 1.2e$^6$ | 2.0e$^{-4}$ | 175 pm | 0.391 |
| scFv | 1.2e$^6$ | 1.7e$^{-4}$ | 141 pm | 0.353 |

Among a plurality of scFv peptides against B7-H4 having various random sequence cassettes in CDR1-3 of $V_H$ and CDR3 of $V_L$, the inventors examined whether similarities in specific domains (specific random sequence cassettes) may render the scFv peptides to have similar binding characteristics to the ligand. Five scFv peptides (801, 802, 905, 906, and 817) were examined for their binding affinities to B7-H4. Among those, as shown in Table 4, four scFv peptides (clone 801, 802, 905, 906) have similar CDR3 sequences. Those four scFv peptides having similar random sequence cassettes in CDR3 of $V_H$ show similar binding affinities to B7-H4 (as shown in Table 5) in both 25° C. and 37° C., indicating that at least in scFv peptides against B7-H4, sequences in CDR3 of $V_H$ may be critical in binding to the ligand.

TABLE 4

| Clone | CDR1 | CDR2 | CDR3 | CDR L3 |
|---|---|---|---|---|
| 801 | NSYAMH (SEQ ID NO: 26) | AISGNGGSTR (SEQ ID NO: 27) | DRFRKVHG (SEQ ID NO: 28) | DATFPL (SEQ ID NO: 29) |
| 802 | GSYAMH (SEQ ID NO: 30) | AISGSGGSTR (SEQ ID NO: 31) | DLYRRVHG (SEQ ID NO: 32) | DYGFPL (SEQ ID NO: 33) |
| 905 | SSYLMH (SEQ ID NO: 34) | VISGSGGSTR (SEQ ID NO: 35) | DLYRRVAG (SEQ ID NO: 36) | DYALPL (SEQ ID NO: 37) |
| 906 | SNYAMH (SEQ ID NO: 38) | AISGNGGSTH (SEQ ID NO: 39) | DRFRRVYG (SEQ ID NO: 40) | DYTFPL (SEQ ID NO: 41) |
| 817 | SSYAMH (SEQ ID NO: 42) | AISGSGGSTR (SEQ ID NO: 43) | GRWSKWG (SEQ ID NO: 44) | TDNFPY (SEQ ID NO: 45) |

TABLE 5

| Temp | scFv | ka | kd | KD |
|---|---|---|---|---|
| 25° C. | 801 | 1.20E+06 | 2.00E−04 | 174 pM |
|  | 802 | 4.50E+05 | 2.40E−05 | 54 pM |
|  | 905 | 4.10E+05 | 1.20E−04 | 290 pM |
|  | 906 | 1.70E+05 | 1.00E−05 | 59 pM |
| 37° C. | 801 | 6.10E+05 | 7.30E−04 | 1.2 nM |
|  | 802 | 5.70E+05 | 5.50E−04 | 1.0 nM |
|  | 905 | 5.80E+05 | 9.70E−04 | 1.7 nM |
|  | 906 | 2.80E+05 | 3.80E−04 | 1.4 nM |

The inventors also generated a plurality of scFv peptides binding to interleukin-8 (IL-8) (scFv IL-8) using the sub-libraries and expression library, and examined the affinity to IL-8 in different conditions (temperatures and pH). Exemplary scFv IL-8 peptides and their binding affinities measured in various conditions are shown in Table 6. Among the clones shown in Table 6, clones 49-7, 49-1 and 49-12 contain similar $V_H$ CDR3 sequences, and clones 49-19, 49-37, and 49-25 contain similar $V_H$ CDR3 sequences. In addition, clones 49-3 and 43-2 contain similar $V_H$ CDR3 sequences. In contrast to the scFv peptides against B7-H4, the inventors found that the binding affinity of scFv IL-8 peptides may not be critically dependent on the similarities in random sequences in CDR3 of $V_H$. For example, while clone 49-18, 49-37, and 49-25 contain similar $V_H$ CDR3 sequences, the binding affinity (unit measured in $K_D \times 10^{-9}$ M) of those sequences varies between $0.894 \times 10^{-9}$ M and $25 \times 10^{-9}$ M.

TABLE 6

| clone | count | 25° C. | pH 6 | 25° C. | pH 6 | 37° C. |
|---|---|---|---|---|---|---|
| 49-31 | 1/36 | 0.012 | 0.0025 |  |  |  |
| 49-22 | 3/36 | 0.113 | 0.328 |  |  |  |
| 49-7 | 1/36 | 0.166 | 0.462 |  |  |  |
| 49-32 | 1/36 | 0.239 | 0.714 |  |  |  |
| 49-34 | 1/36 | 0.618 | 0.342 |  |  |  |
| 49-18 | 1/36 | 0.894 | 2.23 |  |  |  |
| 49-3 | 4/36 | 1.26 | 6.68 | 2.14 | 3.14 | 9.19 |
| 43-2 | 5/16 | 1.41 | 1.3 | 0.79 | 0.96 | 0.89 |
| 49-37 | 1/36 | 1.46 | 4.01 |  |  |  |
| 43-12 | 3/16 | 1.5 | 11.04 |  |  |  |
| 49-10 | 6/36 | 1.65 | 8.58 | 2.21 | 8.7 | 3.45 |
| 49-1 | 1/36 | 2.66 | 6.13 |  |  |  |
| 49-6 | 1/36 | 4.8 | 17.6 |  |  |  |
| 49-12 | 3/36 | 10.1 | 11.9 |  |  |  |
| 49-25 | 2/36 | 25 | 7.26 |  |  |  |

Figure 11:
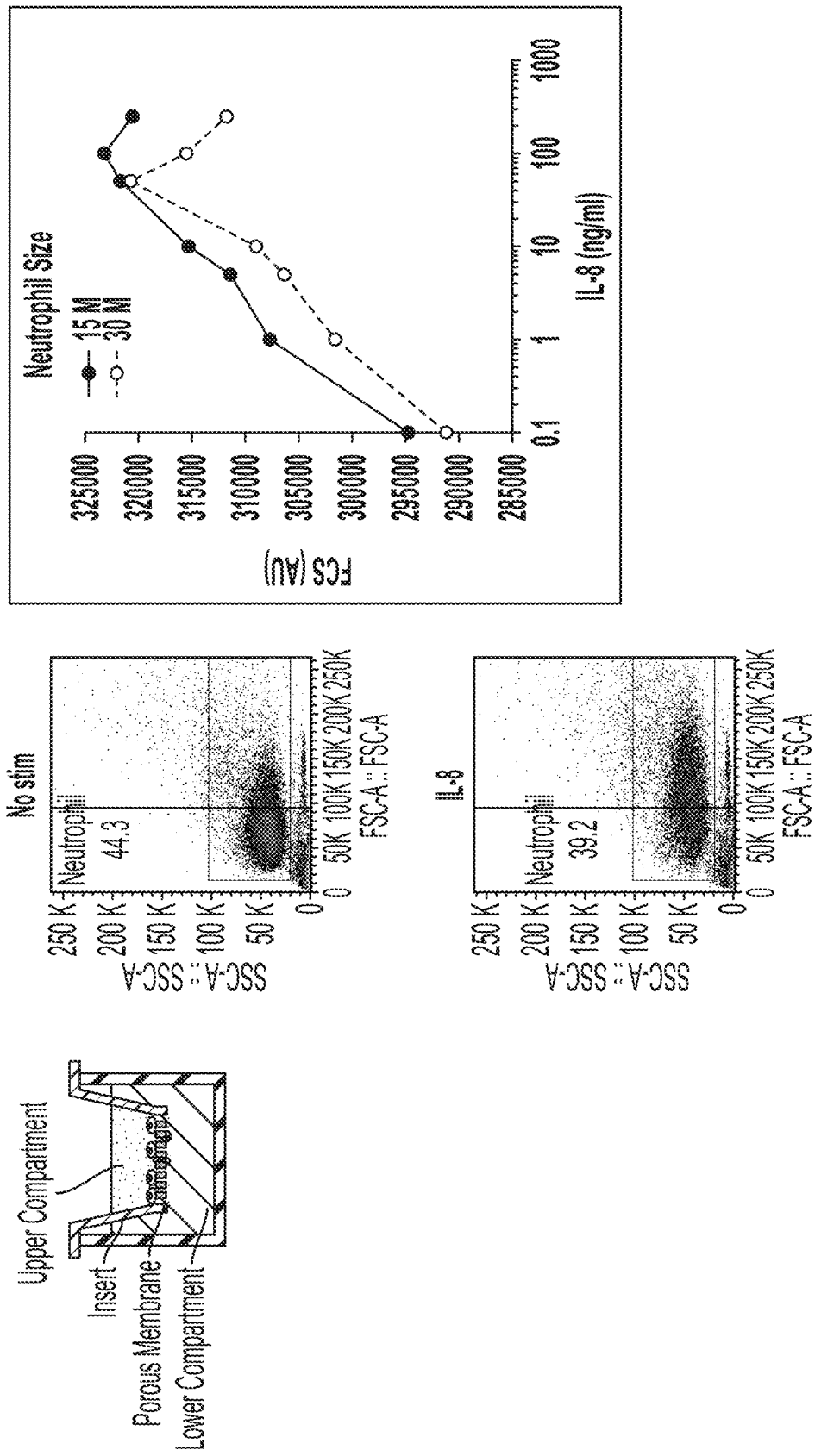
FIG. 11 shows an IL-8 activity assay and its result by measuring neutrophil size changes.
Figure 12:
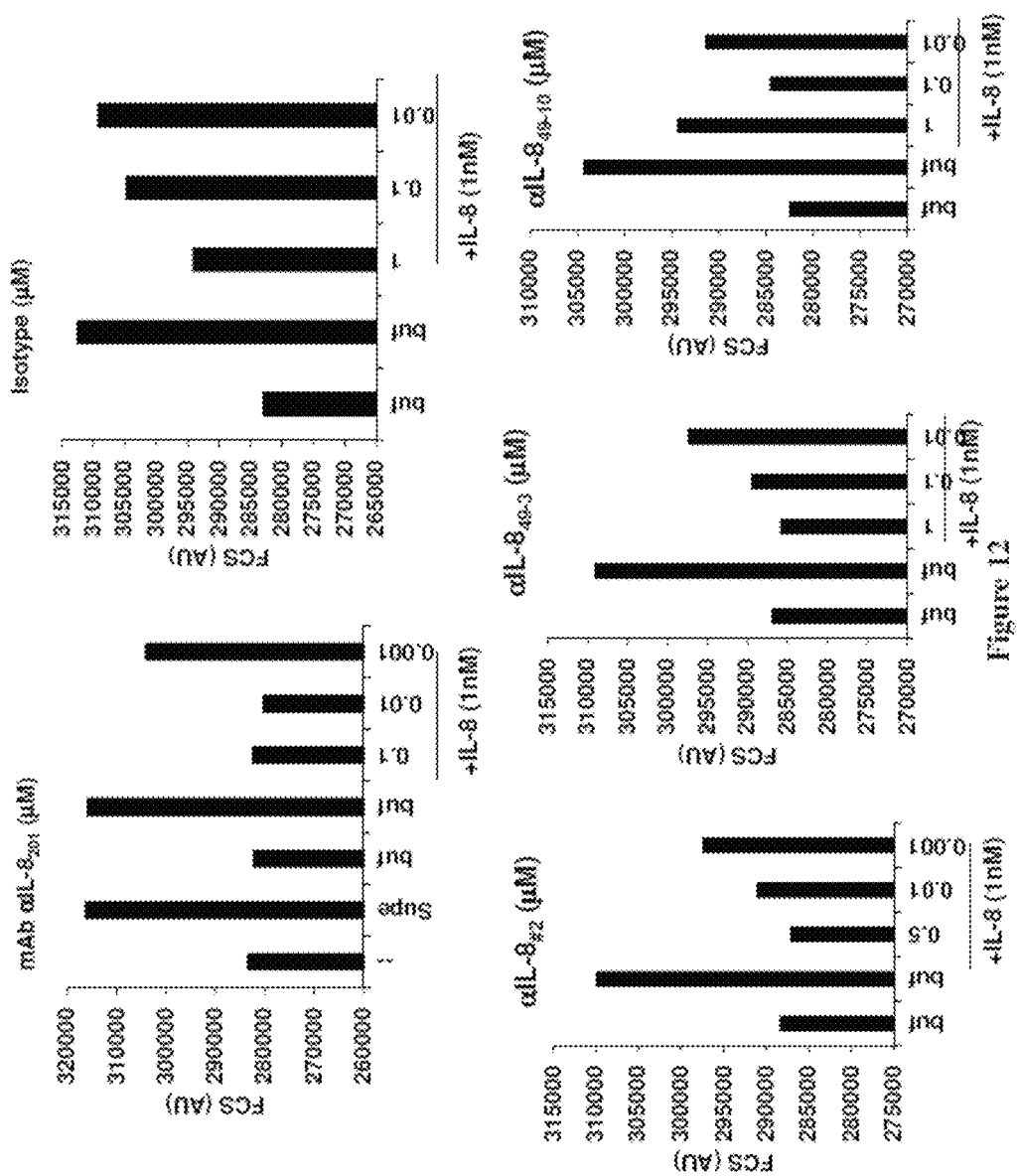
FIG. 12 shows bar graphs indicating neutralization effect of $\alpha$IL-8 antibody to IL-8 activity of increasing neutrophil size.

The inventors further tested whether the scFv IL-8 can effectively trap IL-8 to thereby neutralize the effect of IL-8 by measuring neutrophil size. Generally, neutrophils are enlarged (e.g., having a larger diameter, etc.) upon being stimulated by IL-8 (as shown in FIG. 11). The inventors found that such IL-8 effect on neutrophil enlargement could be largely abolished upon addition of the recombinant α-IL-8 antibody (mAb αIL-8201, as shown in FIG. 12, upper-left graph) or several scFv IL-8 peptides (αIL-8$_{\#2}$, αIL-8$_{49-3}$, αIL-8$_{49-10}$, as shown in FIG. 12, lower graphs), indicating that the scFv IL-8 peptides could effectively neutralize the effect of IL-8 by binding to free IL-8 in the media.

Figure 13:
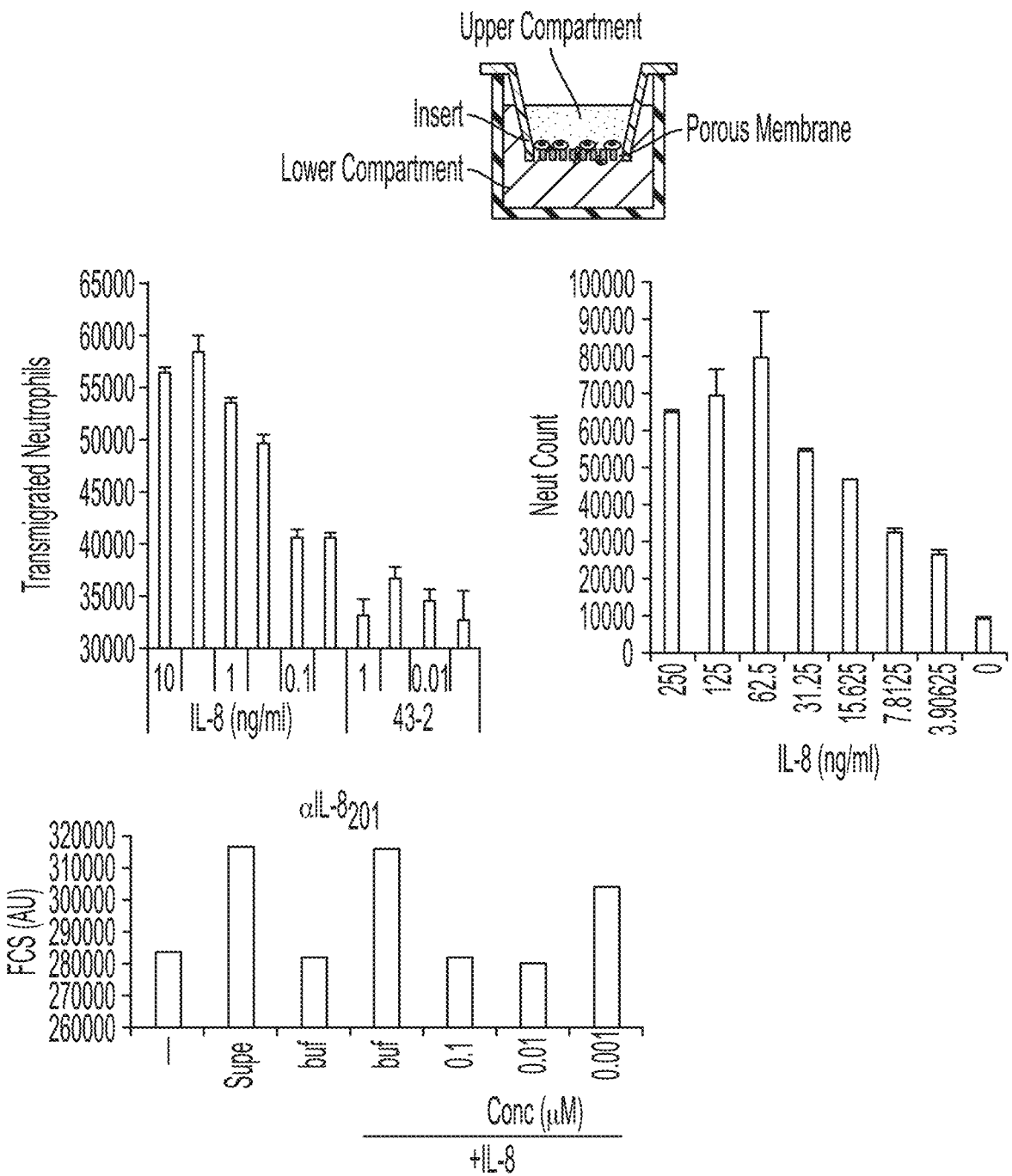
FIG. 13 shows IL-8 activity assay and its results shown in bar graph indicating neutralization effect of $\alpha$IL-8 antibody to IL-8 activity by inhibiting neutrophil migration.

IL-8 is a neutrophil chemotactic factor that causes neutrophils to migrate toward the site of IL-8 release (e.g., site of infection). In order to evaluate the functional effect of scFv IL-8 peptides, neutrophils were placed on the bottom of the insert having a porous membrane and placed in the media including various concentration of IL-8 such that attracted neutrophils by IL-8 can trans-migrate out of the insert through the porous membrane toward the media. As shown in FIG. 13, number of migrated neutrophils increased by increasing IL-8 concentration in the media. Interestingly, such IL-8 effect has almost completely abolished upon addition of the scFv IL-8 peptide (αIL-8$_{43-2}$) or the recombinant IL-8 antibody derived from a scFv IL-8 peptide (mAb αIL-8201).

Figure 14:
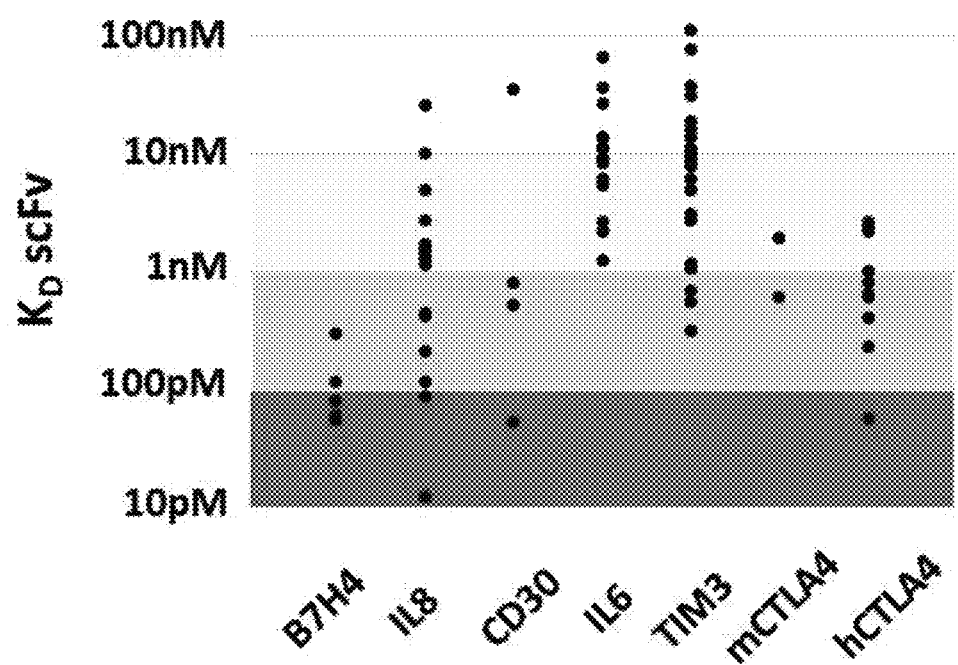
FIG. 14 shows exemplary results using mRNA display library compositions presented herein with respect to selected antigen targets.
Figure 15:
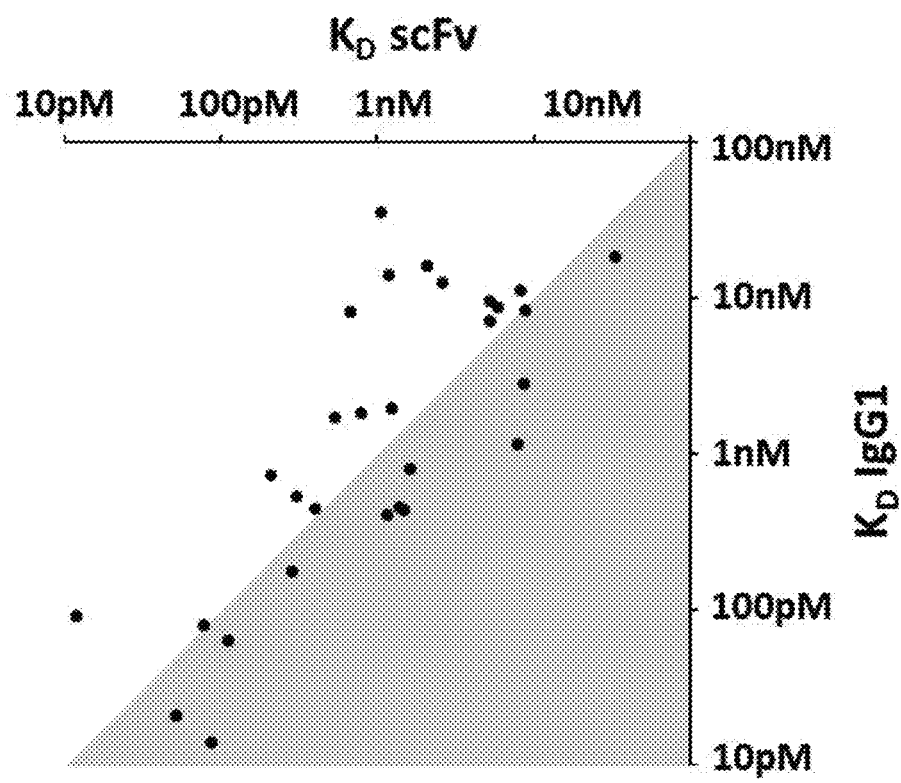
FIG. 15 shows an exemplary graph depicting affinities of selected binders configured as scFv versus IgG where the binders were identified using mRNA display library compositions presented herein.

FIG. 14 depicts further experimental data for a variety of scFvs isolated using the mRNA display library as presented herein. More specifically, each data point represents an scFv for the target indicated at the bottom, and affinity values for each scFv was determined. As can be readily seen, the (same) library yielded multiple high-affinity binders for a variety of distinct targets, with all of the bonders in the sub-microM, and many in the sub-nanoM affinity range. Moreover, the inventors also studies whether the affinity of the scFvs could be preserved upon CDR grafting onto a human IgG. FIG. 15 depicts exemplary results for 29 CDR grafting experiments for selected scFv that were grafted into a human IgG1 scaffold. As can be seen from the results in FIG. 15, the humanized IgG1 antibodies retained high specificity and affinity (typically within one order of magnitude).

It should be apparent to those skilled in the art that many more modifications besides those already described are possible without departing from the inventive concepts herein. The inventive subject matter, therefore, is not to be restricted except in the scope of the appended claims.

Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Where the specification claims refers to at least one of something selected from the group consisting of A, B, C . . . and N, the text should be interpreted as requiring only one element from the group, not A plus N, or B plus N, etc.

What is claimed is:

1. A high-diversity nucleic acid library composition having a plurality of library members, each library member comprising:
    a recombinant nucleic acid comprising a plurality of random cassettes, each having a plurality of degenerate base positions;
    wherein the plurality of random cassettes are derived from at least two members from any of two libraries from the following: (1) a $V_H$-CDR1/2 sub-library, (2) a plurality of $V_H$-CDR3 sub-libraries, and (3) a $V_L$ sub-library; and
    wherein each of the sub-libraries comprises a plurality of members.

2. The composition of claim 1, wherein the plurality of members of the $V_H$-CDR1/2 sub-library comprises a random cassette corresponding to at least one of a portion of $V_H$ CDR1 and at a portion of $V_H$ CDR2.

3. The composition of claim 1, wherein the plurality of the members of the $V_H$-CDR3 sub-libraries comprises a random cassette corresponding to at least a portion of $V_H$ CDR3.

4. The composition of claim 1, wherein the plurality of the members of the $V_L$ sub-library comprises a random cassette at a portion of $V_L$ CDR3.

5. The composition of claim 1, wherein the random cassette is generated using an oligonucleotide selected from SEQ ID NO:1-SEQ ID NO:25.

* * * * *

```
                          SEQUENCE LISTING

<160> NUMBER OF SEQ ID NOS: 45

<210> SEQ ID NO 1
    <211> LENGTH: 58
    <212> TYPE: DNA
    <213> ORGANISM: Artificial Sequence
    <220> FEATURE:
    <223> OTHER INFORMATION: Artificial Sequence for VH CDR1

<400> SEQUENCE: 1
ggcttaggtc tcatttcrvt agttacgcta tgcattgggc gagacgaggt ctgaacgg         58

<210> SEQ ID NO 2
    <211> LENGTH: 58
    <212> TYPE: DNA
    <213> ORGANISM: Artificial Sequence
    <220> FEATURE:
    <223> OTHER INFORMATION: Artificial Sequence for VH CDR1

<400> SEQUENCE: 2
ggcttaggtc tcatttctct rvktacgcta tgcattgggc gagacgaggt ctgaacgg         58

<210> SEQ ID NO 3
    <211> LENGTH: 58
    <212> TYPE: DNA
    <213> ORGANISM: Artificial Sequence
    <220> FEATURE:
    <223> OTHER INFORMATION: Artificial Sequence for VH CDR1

<400> SEQUENCE: 3
ggcttaggtc tcatttctct agttackkga tgcattgggc gagacgaggt ctgaacgg         58

<210> SEQ ID NO 4
    <211> LENGTH: 58
    <212> TYPE: DNA
    <213> ORGANISM: Artificial Sequence
    <220> FEATURE:
    <223> OTHER INFORMATION: Artificial Sequence for VH CDR1

<400> SEQUENCE: 4
ggcttaggtc tcatttctct agttacwmta tgcattgggc gagacgaggt ctgaacgg         58

<210> SEQ ID NO 5
    <211> LENGTH: 58
    <212> TYPE: DNA
    <213> ORGANISM: Artificial Sequence
    <220> FEATURE:
```

<223> OTHER INFORMATION: Artificial Sequence for VH CDR1

<400> SEQUENCE: 5
ggcttaggtc tcatttctct agttacgcta tgavttgggc gagacgaggt ctgaacgg         58

<210> SEQ ID NO 6
<211> LENGTH: 54
<212> TYPE: DNA
<213> ORGANISM: Artificial Sequence
<220> FEATURE:
<223> OTHER INFORMATION: Artificial Sequence for VH CDR2-n

<400> SEQUENCE: 6
ggcttaggtc tcgttcathc attagtggta gtggacgaga cgaggtctga acgg         54

<210> SEQ ID NO 7
<211> LENGTH: 54
<212> TYPE: DNA
<213> ORGANISM: Artificial Sequence
<220> FEATURE:
<223> OTHER INFORMATION: Artificial Sequence for VH CDR2-n

<400> SEQUENCE: 7
ggcttaggtc tcgttcavkt attagtggta gtggacgaga cgaggtctga acgg         54

<210> SEQ ID NO 8
<211> LENGTH: 54
<212> TYPE: DNA
<213> ORGANISM: Artificial Sequence
<220> FEATURE:
<223> OTHER INFORMATION: Artificial Sequence for VH CDR2-n

<400> SEQUENCE: 8
ggcttaggtc tcgttcagct attygggta gtggacgaga cgaggtctga acgg         54

<210> SEQ ID NO 9
<211> LENGTH: 54
<212> TYPE: DNA
<213> ORGANISM: Artificial Sequence
<220> FEATURE:
<223> OTHER INFORMATION: Artificial Sequence for VH CDR2-n

<400> SEQUENCE: 9
ggcttaggtc tcgttcagct attdatggta atggacgaga cgaggtctga acgg         54

<210> SEQ ID NO 10
<211> LENGTH: 54
<212> TYPE: DNA
<213> ORGANISM: Artificial Sequence
<220> FEATURE:
<223> OTHER INFORMATION: Artificial Sequence for VH CDR2-n

<400> SEQUENCE: 10
ggcttaggtc tcgttcagct attagtwmta gtggacgaga cgaggtctga acgg         54

<210> SEQ ID NO 11
<211> LENGTH: 54
<212> TYPE: DNA
<213> ORGANISM: Artificial Sequence
<220> FEATURE:
<223> OTHER INFORMATION: Artificial Sequence for VH CDR2-n

<400> SEQUENCE: 11
ggcttaggtc tcgttcagct attagtkgga gtggacgaga cgaggtctga acgg         54

<210> SEQ ID NO 12
<211> LENGTH: 54
<212> TYPE: DNA
<213> ORGANISM: Artificial Sequence
<220> FEATURE:
<223> OTHER INFORMATION: Artificial Sequence for VH CDR2-n

<400> SEQUENCE: 12
ggcttaggtc tcgttcagct attagtggtr rtggacgaga cgaggtctga acgg    54

<210> SEQ ID NO 13
<211> LENGTH: 52
<212> TYPE: DNA
<213> ORGANISM: Artificial Sequence
<220> FEATURE:
<223> OTHER INFORMATION: Artificial Sequence for VH CDR2-c

<400> SEQUENCE: 13
ggcttaggtc tcgtggarvk agtacttact acgcgagacg aggtctgaac gg    52

<210> SEQ ID NO 14
<211> LENGTH: 52
<212> TYPE: DNA
<213> ORGANISM: Artificial Sequence
<220> FEATURE:
<223> OTHER INFORMATION: Artificial Sequence for VH CDR2-c
<220> FEATURE:
<221> NAME/KEY: misc_feature
<222> LOCATION: (21)..(21)
<223> OTHER INFORMATION: n is a, c, g, or t

<400> SEQUENCE: 14
ggcttaggtc tcgtggaggt natacttact acgcgagacg aggtctgaac gg    52

<210> SEQ ID NO 15
<211> LENGTH: 52
<212> TYPE: DNA
<213> ORGANISM: Artificial Sequence
<220> FEATURE:
<223> OTHER INFORMATION: Artificial Sequence for VH CDR2-c

<400> SEQUENCE: 15
ggcttaggtc tcgtggaggt rvaacttact acgcgagacg aggtctgaac gg    52

<210> SEQ ID NO 16
<211> LENGTH: 52
<212> TYPE: DNA
<213> ORGANISM: Artificial Sequence
<220> FEATURE:
<223> OTHER INFORMATION: Artificial Sequence for VH CDR2-c

<400> SEQUENCE: 16
ggcttaggtc tcgtggaggt agtactvrtt acgcgagacg aggtctgaac gg    52

<210> SEQ ID NO 17
<211> LENGTH: 53
<212> TYPE: DNA
<213> ORGANISM: Artificial Sequence
<220> FEATURE:
<223> OTHER INFORMATION: Artificial Sequence for VH CDR3
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 17
ggcttaggtc tctccgtgrt ckcnnkngst ttcgcgagac gaggtctgaa cgg　　　　　53

<210> SEQ ID NO 18
<211> LENGTH: 58
<212> TYPE: DNA
<213> ORGANISM: Artificial Sequence
<220> FEATURE:
<223> OTHER INFORMATION: Artificial Sequence for VL CDR3

<400> SEQUENCE: 18
ggcttaggtc tctgcagdsg dmtrvtdsgc cttwcacttc gagacgaggt ctgaacgg　　58

<210> SEQ ID NO 19
<211> LENGTH: 58
<212> TYPE: DNA
<213> ORGANISM: Artificial Sequence
<220> FEATURE:
<223> OTHER INFORMATION: Artificial Sequence for VL CDR3

<400> SEQUENCE: 19
ggcttaggtc tctgcagbwt dmtrvtdsgc cttwcacttc gagacgaggt ctgaacgg　　58

<210> SEQ ID NO 20
<211> LENGTH: 58
<212> TYPE: DNA
<213> ORGANISM: Artificial Sequence
<220> FEATURE:
<223> OTHER INFORMATION: Artificial Sequence for VL CDR3
<220> FEATURE:
<221> NAME/KEY: misc_feature
<222> LOCATION: (27)..(27)
<223> OTHER INFORMATION: n is a, c, g, or t

<400> SEQUENCE: 20
ggcttaggtc tctgcagdsg dmtrvtnwtc cttwcacttc gagacgaggt ctgaacgg　　58

<210> SEQ ID NO 21
<211> LENGTH: 58
<212> TYPE: DNA
<213> ORGANISM: Artificial Sequence
<220> FEATURE:
<223> OTHER INFORMATION: Artificial Sequence for VL CDR3
<220> FEATURE:
<221> NAME/KEY: misc_feature
<222> LOCATION: (27)..(27)
<223> OTHER INFORMATION: n is a, c, g, or t

<400> SEQUENCE: 21
ggcttaggtc tctgcagbwt dmtrvtnwtc cttwcacttc gagacgaggt ctgaacgg　　58

<210> SEQ ID NO 22
<211> LENGTH: 58
<212> TYPE: DNA
<213> ORGANISM: Artificial Sequence
<220> FEATURE:
<223> OTHER INFORMATION: Artificial Sequence for VL CDR3

<400> SEQUENCE: 22
ggcttaggtc tctgcagdsg dmtrvtdsgc ctykgacttc gagacgaggt ctgaacgg　　58

<210> SEQ ID NO 23
<211> LENGTH: 58
<212> TYPE: DNA
<213> ORGANISM: Artificial Sequence
<220> FEATURE:
<223> OTHER INFORMATION: Artificial Sequence for VL CDR3

<400> SEQUENCE: 23
ggcttaggtc tctgcagbwt dmtrvtdsgc ctykgacttc gagacgaggt ctgaacgg        58

<210> SEQ ID NO 24
<211> LENGTH: 58
<212> TYPE: DNA
<213> ORGANISM: Artificial Sequence
<220> FEATURE:
<223> OTHER INFORMATION: Artificial Sequence for VL CDR3
<220> FEATURE:
<221> NAME/KEY: misc_feature
<222> LOCATION: (27)..(27)
<223> OTHER INFORMATION: n is a, c, g, or t

<400> SEQUENCE: 24
ggcttaggtc tctgcagdsg dmtrvtnwtc ctykgacttc gagacgaggt ctgaacgg        58

<210> SEQ ID NO 25
<211> LENGTH: 58
<212> TYPE: DNA
<213> ORGANISM: Artificial Sequence
<220> FEATURE:
<223> OTHER INFORMATION: Artificial Sequence for VL CDR3
<220> FEATURE:
<221> NAME/KEY: misc_feature
<222> LOCATION: (27)..(27)
<223> OTHER INFORMATION: n is a, c, g, or t

<400> SEQUENCE: 25
ggcttaggtc tctgcagbwt dmtrvtnwtc ctykgacttc gagacgaggt ctgaacgg        58

<210> SEQ ID NO 26
<211> LENGTH: 6
<212> TYPE: PRT
<213> ORGANISM: Artificial Sequence
<220> FEATURE:
<223> OTHER INFORMATION: Clone 801 CDRH1

<400> SEQUENCE: 26

Asn Ser Tyr Ala Met His
1               5

<210> SEQ ID NO 27
<211> LENGTH: 10
<212> TYPE: PRT
<213> ORGANISM: Artificial Sequence
<220> FEATURE:
<223> OTHER INFORMATION: Clone 801 CDRH2

<400> SEQUENCE: 27

Ala Ile Ser Gly Asn Gly Gly Ser Thr Arg
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Clone 801 CDRH3

<400> SEQUENCE: 28

Asp Arg Phe Arg Lys Val His Gly
1               5

<210> SEQ ID NO 29
<211> LENGTH: 6

```
<212> TYPE: PRT
<213> ORGANISM: Artificial Sequence
<220> FEATURE:
<223> OTHER INFORMATION: Clone 801 CDRL3

<400> SEQUENCE: 29

Asp Ala Thr Phe Pro Leu
1               5

<210> SEQ ID NO 30
<211> LENGTH: 6
<212> TYPE: PRT
<213> ORGANISM: Artificial Sequence
<220> FEATURE:
<223> OTHER INFORMATION: Clone 802 CDRH1

<400> SEQUENCE: 30

Gly Ser Tyr Ala Met His
1               5

<210> SEQ ID NO 31
<211> LENGTH: 10
<212> TYPE: PRT
<213> ORGANISM: Artificial Sequence
<220> FEATURE:
<223> OTHER INFORMATION: Clone 802 CDRH2

<400> SEQUENCE: 31

Ala Ile Ser Gly Ser Gly Gly Ser Thr Arg
1               5                   10

<210> SEQ ID NO 32
<211> LENGTH: 8
<212> TYPE: PRT
<213> ORGANISM: Artificial Sequence
<220> FEATURE:
<223> OTHER INFORMATION: Clone 802 CDRH3

<400> SEQUENCE: 32

Asp Leu Tyr Arg Arg Val His Gly
1               5

<210> SEQ ID NO 33
<211> LENGTH: 6
<212> TYPE: PRT
<213> ORGANISM: Artificial Sequence
<220> FEATURE:
<223> OTHER INFORMATION: Clone 802 CDRL3

<400> SEQUENCE: 33

Asp Tyr Gly Phe Pro Leu
1               5

<210> SEQ ID NO 34
<211> LENGTH: 6
<212> TYPE: PRT
<213> ORGANISM: Artificial Sequence
<220> FEATURE:
<223> OTHER INFORMATION: Clone 905 CDRH1

<400> SEQUENCE: 34

Ser Ser Tyr Leu Met His
1               5

<210> SEQ ID NO 35
<211> LENGTH: 10
<212> TYPE: PRT
```

```
<213> ORGANISM: Artificial Sequence
<220> FEATURE:
<223> OTHER INFORMATION: Clone 905 CDRH2

<400> SEQUENCE: 35

Val Ile Ser Gly Ser Gly Gly Ser Thr Arg
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Clone 905 CDRH3

<400> SEQUENCE: 36

Asp Leu Tyr Arg Arg Val Ala Gly
1               5

<210> SEQ ID NO 37
<211> LENGTH: 6
<212> TYPE: PRT
<213> ORGANISM: Artificial Sequence
<220> FEATURE:
<223> OTHER INFORMATION: Clone 905 CDRL3

<400> SEQUENCE: 37

Asp Tyr Ala Leu Pro Leu
1               5

<210> SEQ ID NO 38
<211> LENGTH: 6
<212> TYPE: PRT
<213> ORGANISM: Artificial Sequence
<220> FEATURE:
<223> OTHER INFORMATION: Clone 906 CDRH1

<400> SEQUENCE: 38

Ser Asn Tyr Ala Met His
1               5

<210> SEQ ID NO 39
<211> LENGTH: 10
<212> TYPE: PRT
<213> ORGANISM: Artificial Sequence
<220> FEATURE:
<223> OTHER INFORMATION: Clone 906 CDRH2

<400> SEQUENCE: 39

Ala Ile Ser Gly Asn Gly Gly Ser Thr His
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Clone 906 CDRH3

<400> SEQUENCE: 40

Asp Arg Phe Arg Arg Val Tyr Gly
1               5

<210> SEQ ID NO 41
<211> LENGTH: 6
<212> TYPE: PRT
<213> ORGANISM: Artificial Sequence
```

```
<220> FEATURE:
<223> OTHER INFORMATION: Clone 906 CDRL3

<400> SEQUENCE: 41

Asp Tyr Thr Phe Pro Leu
1               5

<210> SEQ ID NO 42
<211> LENGTH: 6
<212> TYPE: PRT
<213> ORGANISM: Artificial Sequence
<220> FEATURE:
<223> OTHER INFORMATION: Clone 817 CDRH1

<400> SEQUENCE: 42

Ser Ser Tyr Ala Met His
1               5

<210> SEQ ID NO 43
<211> LENGTH: 10
<212> TYPE: PRT
<213> ORGANISM: Artificial Sequence
<220> FEATURE:
<223> OTHER INFORMATION: Clone 817 CDRH2

<400> SEQUENCE: 43

Ala Ile Ser Gly Ser Gly Gly Ser Thr Arg
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Clone 817 CDRH3

<400> SEQUENCE: 44

Gly Arg Trp Ser Lys Trp Gly
1               5

<210> SEQ ID NO 45
<211> LENGTH: 6
<212> TYPE: PRT
<213> ORGANISM: Artificial Sequence
<220> FEATURE:
<223> OTHER INFORMATION: Clone 817 CDRL3

<400> SEQUENCE: 45

Thr Asp Asn Phe Pro Tyr
1               5
```